(12) United States Patent
Hidaka et al.

(10) Patent No.: US 8,167,589 B2
(45) Date of Patent: May 1, 2012

(54) ARTIFICIAL HEART PUMP WITH ADJUSTABLE MAGNETIC THRUST BEARING

(75) Inventors: Tatsuya Hidaka, Takasago (JP); Yohei Kakiuchi, Takasago (JP); Takeshi Okubo, Takasago (JP); Toshiyuki Osada, Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 1229 days.

(21) Appl. No.: 11/918,906

(22) PCT Filed: Aug. 17, 2006

(86) PCT No.: PCT/JP2006/316162
§ 371 (c)(1),
(2), (4) Date: Oct. 19, 2007

(87) PCT Pub. No.: WO2007/020972
PCT Pub. Date: Feb. 22, 2007

(65) Prior Publication Data
US 2009/0306771 A1     Dec. 10, 2009

(30) Foreign Application Priority Data

Aug. 19, 2005  (JP) .................................. 2005-238909
Sep. 13, 2005  (JP) .................................. 2005-265686

(51) Int. Cl.
F04B 35/04 (2006.01)
(52) U.S. Cl. .................................. 417/423.14; 417/356
(58) Field of Classification Search .................. 417/355, 417/356, 423.1, 423.12, 423.14; 415/10, 415/104, 107, 131, 132, 174.1, 229, 900; 600/16; 604/6.11; 310/90, 90.5
See application file for complete search history.

(56) References Cited

U.S. PATENT DOCUMENTS

| | | | |
|---|---|---|---|
| 3,249,777 A * | 5/1966 | Congdon et al. ............... | 310/104 |
| 3,559,772 A * | 2/1971 | Grombka ....................... | 188/170 |
| 4,994,078 A | 2/1991 | Jarvik | |
| 5,588,812 A | 12/1996 | Taylor et al. | |
| 5,692,882 A | 12/1997 | Bozeman et al. | |
| 6,050,975 A | 4/2000 | Poirier | |
| 6,123,659 A | 9/2000 | le Blanc et al. | |

(Continued)

FOREIGN PATENT DOCUMENTS

JP     2001-514532 A     9/2001

(Continued)

OTHER PUBLICATIONS

Machine Language Translation of Japanese Patent Application JP 2004346930 A listed in applicant's IDS filed Oct. 19, 2007.*

(Continued)

*Primary Examiner* — Devon C Kramer
*Assistant Examiner* — Dnyanesh Kasture
(74) *Attorney, Agent, or Firm* — Birch, Stewart, Kolasch & Birch, LLP

(57) ABSTRACT

In order to optimize the clearances between both end surfaces of a sleeve 5 and each of the end surfaces of the fixed bodies 3 and 5, respectively, magnetic forces of repulsion being caused by each of the permanent magnets 3a, 5b, 5c and 8a is adjusted. At this time, by adjusting each of the distances between the permanent magnets 3a, 5b, 5c, 8a, respectively, by adjusting the quantity of the adjustment rings 9, the magnetic force of repulsion being caused by each of the permanent magnets 3a, 5b, 5c and 8a is adjusted.

14 Claims, 17 Drawing Sheets

U.S. PATENT DOCUMENTS

| | | | |
|---|---|---|---|
| 6,227,820 B1 * | 5/2001 | Jarvik | 417/423.12 |
| 6,527,699 B1 | 3/2003 | Goldowsky | |
| 6,719,791 B1 | 4/2004 | Nüsser et al. | |
| 2003/0163019 A1 | 8/2003 | Goldowsky | |
| 2004/0241019 A1 * | 12/2004 | Goldowsky | 417/423.1 |
| 2005/0035681 A1 * | 2/2005 | Faltin | 310/268 |

FOREIGN PATENT DOCUMENTS

| | | |
|---|---|---|
| JP | 2003-503639 A | 1/2003 |
| JP | 2004-329236 A | 11/2004 |
| JP | 2004-346930 A | 12/2004 |
| JP | 2004-351213 A | 12/2004 |
| JP | 2005-28156 A | 2/2005 |
| JP | 2005-58617 A | 3/2005 |
| WO | 97/49440 A2 | 12/1997 |
| WO | WO-01/02724 A1 | 1/2001 |

OTHER PUBLICATIONS

Machine Translation of Japanese Patent JP 2004346930 A provided in applicant's IDS of Oct. 19, 2007.*

"The Engineers Sketch-Book of Mechanical Movements, Devices, Appliances, Contrivances, and Details", Author: Thomas Walter Barber, Relevant pp. 168-173, Published in 1948.*

* cited by examiner

ARTIFICIAL HEART PUMP WITH ADJUSTABLE MAGNETIC THRUST BEARING

BACKGROUND OF THE INVENTION

1. Field of the Invention

The present invention relates to an artificial heart pump and especially relates to an artificial heart pump employing an axial-flow turbo pump that pumps the blood.

2. Description of the Related Art

Conventionally, an artificial heart pump which pumps the blood by utilizing the rotation of the impellers is employed as an alternate being used for medical purposes or as an assist pump. An artificial heart pump utilizing a roller pump or a centrifugal pump and an artificial heart pump utilizing an axial-flow turbo pump are provided as the aforementioned artificial heart pump. Among these various types of artificial heart pumps, the artificial heart pump utilizing an axial-flow turbo pump can reduce the size thereof, being compared with the artificial heart pump utilizing a roller pump or a centrifugal pump.

The conventional artificial heart pump utilizing an axial-flow turbo pump has a housing thereof house motor stators, and at the same time, has a rotor being equipped with impellers on the circumference thereof house permanent magnets which react to the motor stators magnetically. As an artificial heart pump that has been described hereinabove, as shown in FIG. 14, such an artificial heart pump is provided as wherein, a rotor 104 being equipped with impellers 105 on the outer circumference surface thereof is installed between fixed bodies 102 and 103 that are fixed to a housing 101; and pivot bearings 106a and 106b are installed to the surfaces where the fixed bodies 102 and 103 face the rotor 104. To be specific, by protruding the centers of the surfaces of the rotor 104 that face the fixed bodies 102 and 103, the pivot bearings 106a and 106b are formed.

In addition, as shown in FIG. 15, by providing the interiors of the fixed bodies 102 and 103 with magnet coils 111 and 112 that generate magnetic force and by providing both ends of the interior of the rotor 104 with permanent magnets 113 and 114 in such a manner as to face the magnet coils 111 and 112, such an artificial heart pump is provided as is equipped with magnetic bearings that support the rotor 104 by magnetic force. In the artificial heart pump shown in FIG. 15, an active magnetic bearing is constructed in a manner that by installing a position sensor 115 to the fixed body 102, the position of the rotor 104 is detected in order to specify the amount of the current of the magnetic coils 111 and 112, so that the rotor 104 will be located at the optimum position.

Moreover, as shown in FIG. 16, such an artificial heart pump is provided as wherein, the fixed bodies 102 and 103 are connected by a fixed shaft 121; and a rotor 122 having a cylindrical shape and rotating along the outer circumference of the fixed shaft 121 is installed; and at the same time, hydrodynamic bearings are constructed by providing a groove to each of the surfaces where the rotor 122 faces the fixed bodies 102 and 103, respectively. To be specific, by having the rotor 122 rotate, the blood flows into minimal gaps being formed by the grooves that are provided to each of the surfaces where the rotor 122 and the fixed bodies 102 and 103 face, respectively, which consequently generates hydrodynamic pressures, thereby preventing the rotor 122 from contacting the fixed bodies 102 and 103 and behaving as a thrust bearing.

However, when the rotor is supported by the pivot bearings 106a and 106b as shown in FIG. 14, abrasion powders are sometimes generated in the pivot bearings 106a and 106b. In addition, because the gaps between the fixed bodies 102 and 103 and the rotor 104 become narrow, there is a possibility that a blood clot may be formed easily or that red blood cells may be destroyed. Moreover, when active magnetic bearings are employed as shown in FIG. 15, non-contact support will be possible, but electric power will be necessary for active control, and in addition, the construction thereof will become complex as well as the equipment will become larger. Furthermore, when the hydrodynamic bearings are constructed as shown in FIG. 16, narrow gaps will be necessary for generating the hydrodynamic pressures, and due to the relevant gaps, there is a possibility that a blood clot may be formed easily or that red blood cells may possibly be destructed.

In order to prevent the above-mentioned problems, the present applicant proposes an artificial heart pump which prevents the rotor from contacting the fixed bodies by passive type of repulsive magnetic bearings, which not only construct the hydrodynamic bearings but also utilize the magnetic force of repulsion balancing the hydro thrust load on the impellers. (See the Patent Literature No. 1.) The artificial heart pump being equipped with the passive type of repulsive magnetic bearings has permanent magnets 131 and 132 installed to each of the rotor 122 and the fixed body 103 having the construction being shown in FIG. 16, as shown in FIG. 17, thereby having the magnetic force of repulsion balancing the hydro thrust load construct the passive type of repulsive magnetic bearings.

Moreover, such an artificial heart pump is provided as wherein, the artificial heart pump is not only supported by the pivot bearings as shown in FIG. 14 but also axially suspended by providing a permanent magnet to each of the fixed bodies at the front end and the back of the rotor and the rotor, respectively. (See the Patent Literature No. 2.) The artificial heart pump being described hereinabove has permanent magnets installed to the locations of the rotor facing two fixed bodies and to the locations of the two fixed bodies facing the rotor, thereby providing two sets of magnetic forces of repulsion to each of the anterior and the posterior locations of the rotor, respectively, which consequently suspends and supports the rotor.

Patent Literature No. 1: Patent Application Laid Open as 2004-346930

Patent Literature No. 2: Patent Application Laid Open as 2004-351213

SUMMARY OF THE INVENTION

Issues to be Solved by the Present Invention

In case of an artificial heart pump being equipped with passive type of repulsive magnetic bearings as described in the Patent Literature No. 1, gaps can be made wider than an artificial heart pump being equipped only with hydrodynamic bearings as shown in FIG. 16. As a result, occurrence of a blood clot or of the destruction of red blood cells can be reduced, but the rotor portion is made to contact the fixed bodies at the front end and the back of the rotor due to the magnetic force of repulsion, under an operation condition that makes the hydro thrust load small and at the time of start-up or shutdown. Therefore, there are possibilities of generating abrasion powders due to the contact of the rotor with the fixed bodies and of causing a blood clot and destruction of red blood cells.

In addition, in the artificial heart pumps being constructed as in the Patent Literature No. 1 and the Patent Literature No. 2, the positions to install the permanent magnets are fixed. In consequence, in order to optimize the dimensions of the clearances between the rotor and the fixed bodies, it is necessary to provide machining to the rotor and the fixed bodies, respectively, for the purpose of installing the permanent magnets, and it is difficult to control the dimensions by the aforementioned machining.

Means to Solve the Issue

It is an object of the present invention to provide an artificial heart pump which can determine the positions to install the permanent magnets easily in order to obtain the optimum dimensions of the clearances between the rotor and the fixed bodies.

In order to achieve the above-mentioned object, an artificial heart pump in accordance with the present invention comprises: a housing; a fixed shaft being fixed to a center position inside the housing; two fixed bodies being connected to the housing and being connected one to each end of the fixed shaft; a rotating shaft being fitted into the fixed shaft; a plurality of blades protruding from an outside wall surface of the rotating shaft; motor stators being housed at positions surrounding the rotating shaft and generating rotating magnetic fields inside the housing; multi-pole oriented anisotropic permanent magnets being housed inside the rotating shaft and generating a magnetic field being vertical against an outside wall surface of the rotating shaft; a first magnetic-field-generating portion being housed in a vicinity of a connection portion of at least one of the fixed bodies that is connected to the fixed shaft and generating a magnetic field that prevents a contact with the rotating shaft; a second magnetic-field-generating portion being housed in the rotating shaft and generating a magnetic field which reacts together with the first magnetic-field-generating portion, thereby preventing a contact with the fixed bodies; and an adjustment portion which adjusts magnetic forces being generated by the first and the second magnetic-field-generating portions, by adjusting a distance between the first and the second magnetic-field-generating portions.

Effects of Invention

In accordance with the present invention, by having an adjustment portion provided that adjusts a distance between the magnets for the first and the second repulsive magnetic bearings, it is possible to easily adjust the magnetic forces of repulsion being generated on both ends of the rotating shaft by the magnets for the first and the second repulsive magnetic bearings, in order that the rotating shaft and the fixed bodies will not contact each other. In addition, by having the adjustment portion consist of a component that can shift the position to install the magnet for the first repulsive magnetic bearing inside the fixed bodies, it is possible to easily adjust the magnetic forces of repulsion being generated by the magnets for the first and the second repulsive magnetic bearings, without changing the distance between the fixed bodies. Moreover, by having the adjustment portion consist of components that are installed between the fixed shaft and the fixed bodies, it is possible to easily adjust the magnetic force of repulsion being generated on both ends of the rotating shaft.

DESCRIPTION OF REFERENCES NUMERALS

1: Housing
2: Diffuser
3: Fixed body
4: Fixed Shaft
5: Sleeve

6: Impeller
7: Current Plate
8: Fixed body
9: Adjustment Ring
10: Gap Sensor
11: Spacer
12: Adjustment Member

DETAILED DESCRIPTION OF THE INVENTION

[First Embodiment]

Figure 1:
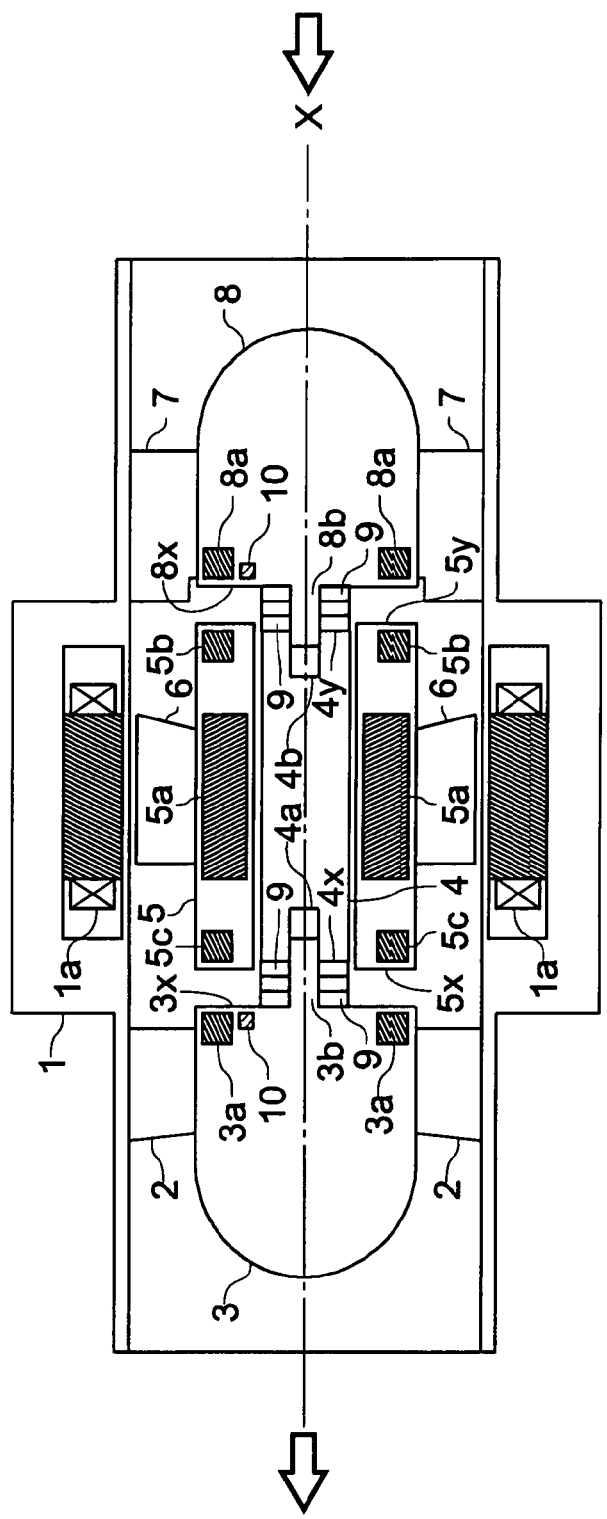
FIG. 1 is a cross-sectional view showing a construction of an artificial heart pump in accordance with a first embodiment of the present invention.

Referring to the drawings, a first embodiment of the present invention will be described hereinafter. FIG. 1 is a cross-sectional view showing a construction of an artificial heart pump in accordance with this embodiment of the present invention. Hereinafter, the words "before/anterior" and "after/posterior" will be referred as the anterior side (upstream-side) and the posterior side (downstream-side) respectively, in accordance with the flow of the blood.

An artificial heart pump in FIG. 1 comprises a cylindrical housing 1; a plurality of diffusers 2 being connected to the inside wall surface of the housing 1; a fixed body 3 being supported by the housing 1 by having a plurality of diffusers 2 protrude from the outside wall surface; a fixed shaft 4 being installed before the fixed body 3; a sleeve 5 being installed circularly around the fixed shaft 4 and rotating around the outer circumference of the fixed shaft 4; a plurality of blades 6 protruding from the outside wall surface of the sleeve 5; a plurality of current plates 7 being installed to more anterior-side than the impellers 6 and being connected to the inside wall surface of the housing 1; and a fixed body 8 being connected to the fixed shaft 4 and being supported by the housing 1 by having the current plates 7 protrude from the outside wall surface.

The artificial heart pump has the inside of the sleeve 5 provided with multi-pole oriented anisotropic permanent magnets 5a as well as has the inside of the housing 1 provided with motor stators 1a consisting of magnet coils that have magnetic poles thereof face the outside wall surface of the sleeve 5. In addition, a plurality of multi-pole oriented anisotropic permanent magnets 5a are provided in a radial pattern with the central axis X of the artificial heart pump serving as the center thereof, wherein, the direction of the magnetic flux thereof is vertical against the inside wall surface of the housing 1. Moreover, the magnetic poles of the adjacent multi-pole oriented anisotropic permanent magnets 5a which face the inside wall surface of the housing 1 is made to be reverse polarity. Consequently, by having electric currents of different phase such as three-phase electric current and the like flow through the magnetic coils consisting the motor stators 1a, rotating motive energy acts on the multi-pole oriented anisotropic permanent magnets 5a, thereby causing the sleeve 5 and the impellers 6 to rotate as a motor rotor.

Then, the anterior tip portion of the sleeve 5 houses a ring-shaped permanent magnet 5b, and at the same time, the fixed body 8 houses a permanent magnet 8a whose posterior surface faces the anterior surface of the permanent magnet 5b. Wherein, because the magnetic pole of the anterior surface of the permanent magnet 5b and the magnetic pole of the posterior surface of the permanent magnet 8a have the same polar character, magnetic forces of repulsion by the permanent magnets 5b and 8a act. In addition, the posterior tip portion of the sleeve 5 houses a ring-shaped permanent magnet 5c, and at the same time, the fixed body 3 houses a permanent magnet 3a whose anterior surface faces the posterior surface of the permanent magnet 5c. Wherein, because the magnetic pole of the posterior surface of the permanent magnet 5c and the magnetic pole of the anterior surface of the permanent magnet 3a have the same polar character, magnetic forces of repulsion by the permanent magnets 5c and 3a act.

The permanent magnets 5b and 8a and the permanent magnets 5c and 3a function as thrust bearings against the axial direction of the central axis X; and the magnetic forces of repulsion by the permanent magnets 5b and 8a and the permanent magnets 5c and 3a, respectively, are adjusted so as to balance the hydro thrust load serving as a force to move the sleeve 5 forward by having the pressure on the posterior side of the impellers become 6 high during operation of the artificial heart pump. In consequence, it is possible to prevent the contact of the posterior end surface 5x of the sleeve 5 with the anterior end surface 3x of the fixed body 3 and the contact of the anterior end surface 5y of the sleeve 5 with the posterior end surface 8x of the fixed body 8 during rotation of the sleeve 5. In addition, during start-ups and shutdowns and under an operation condition that the hydro thrust load is small, by the magnetic forces of repulsion of the permanent magnets 5b and 8a and the permanent magnets 5c and 3a, respectively, it is possible to prevent the contact of the posterior end surface 5x of the sleeve 5 with the anterior end surface 3x of the fixed body 3 and the contact of the anterior end surface 5y of the sleeve 5 with the posterior end surface 8x of the fixed body 8.

Moreover, the current plates 7 having both edges thereof connected to the outside wall surface of the fixed body 8 and to the inside wall surface of the housing 1 are placed circumferentially, being equally spaced, with the central axis X serving as the center, and additionally, the diffusers 2 having both edges thereof connected to the outside wall surface of the fixed body 3 and to the inside wall surface of the housing 1 are placed circumferentially, being equally spaced, with the central axis X serving as the center. Then, each of the anterior edge of the fixed body 8 and the posterior edge of the fixed body 3 has the central portion thereof elevated, respectively. Consequently, the bloods being taken in are diverged without receiving any resistance and led to the current plates 7 by the elevation of the anterior edge of the fixed body 8; and then, the flowing bloods being straightened by the diffusers 2 are joined without receiving any resistance by the elevation of the posterior edge of the fixed body 3.

In addition, the fixed bodies 3 and 8 and the fixed shaft 4 are connected by having the protruding portions 3b and 8b that are provided to the center positions of the end surfaces 3x and 8x, respectively, of the fixed bodies 3 and 8, respectively, inserted into the holes 4a and 4b that are provided to the center positions of both end surfaces 4x and 4y of the fixed shaft 4, respectively. Each of the holes 4a and 4b and each of the protruding portions 3b and 8b are threaded. By having the protruding portions 3b and 8b rotated and inserted into the holes 4a and 4b, the fixed bodies 3 and 8 are fixed to the fixed shaft 4 around which the sleeve 5 is installed circumferentially.

Furthermore, between the anterior end surface 3x of the fixed body 3 and the posterior end surface 4x of the fixed shaft 4, more than one piece of adjustment ring 9 is installed to adjust the clearance between the posterior end surface 5x of the sleeve 5 and the anterior end surface 3x of the fixed body 3; and then, more than one piece of adjustment ring 9 is installed between the posterior end surface 8x of the fixed body 8 and the anterior end surface 4y of the fixed shaft 4 to adjust the clearance between the anterior end surface 5y of the sleeve 5 and the anterior end surface 8x of the fixed body 8. Hereat, the adjustment rings 9 are installed circumferentially around the protruding portions 3b and 8b of the fixed bodies 3 and 8, respectively; and the fixed bodies 3 and 8 around which the adjustment rings 9 are installed circumferentially are inserted into the fixed shaft 4, thereby adjusting the clearances between the fixed bodies 3 and 8 and the sleeve 5.

When the artificial heart pump is constructed as described hereinabove, by performing trial operation and measuring the clearances between the fixed bodies 3 and 8 and the sleeve 5 that are adjusted with the adjustment rings 9 during manufacturing, the clearances between the fixed bodies 3 and 8 and the sleeve 5 are adjusted by using the adjustment rings 9. By the adjustment using the adjustment rings 9, the clearances between the fixed bodies 3 and 8 and the sleeve 5 are adjusted, so as not to have the fixed bodies 3 and 8 and the sleeve 5 contact each other under operation conditions to be applied. Hereat, by having the gap sensors 10 installed inside the fixed body 3 or the fixed body 8, in an end surfaces 3x or 8x side part thereof, as shown in FIG. 1, the clearances between the fixed bodies 3 and 8 and the sleeve 5 are measured during start-ups and shutdowns and under the operation condition that the hydro thrust load is small. Consequently, the clearance between the fixed body 3 and the sleeve 5 is measured by the gap sensor 10 inside the fixed body 3, while the clearance between the fixed body 8 and the sleeve 5 is measured by the gap sensor 10 inside the fixed body 8.

In addition, the gap sensor 10 may be installed to only one of the fixed bodies 3 and 8. To be specific, when the gap sensor 10 is installed inside the fixed body 3, the clearance between the fixed body 3 and the sleeve 5 is measured by the gap sensor 10. Then, the clearance between the fixed body 8 and the sleeve 5 is obtained by the clearance between the fixed body 3 and the sleeve 5 being measured, by the quantity of the adjustment rings 9 being installed and by the axial lengths of the fixed shaft 4 and the sleeve 5.

When the clearances between the fixed bodies 3 and 8 and the sleeve 5 are specified so as to obtain the appropriate dimension, by using the adjustment rings 9, the gap sensor 10 being housed by either of the fixed body 3 or the fixed body 8 may be taken out after removing the fixed body 3 or the fixed body 8 from the fixed shaft 4. Then, the fixed bodies 3 and 8 that have the confirmed quantity of adjustment rings 9 installed circumferentially around the protruding portions 3b and 8b are re-connected to the fixed shaft 4 around which the sleeve 5 is installed circumferentially. In addition, the appropriate dimensions of the clearances between the fixed bodies 3 and 8 and the sleeve 5 may not be measured by the gap sensor 10 but may be measured by externally measuring the contact of the fixed bodies 3 and 8 with the sleeve 5.

Moreover, in accordance with the present embodiment, both of the fixed bodies 3 and 8 are provided with the protruding portions 3b and 8b, and at the same time, have holes 4a and 4b provided to both end surfaces 4x and 4y of the fixed shaft 4. However, one of the fixed bodies 3 and 8 may be provided with the protruding portion, and at the same time, the end surface of the fixed shaft 4 where the fixed body being quipped with a protruding portion is connected may have a hole provided thereto. To be specific, when the fixed body 3 is provided with the protruding portion 3b and the fixed body 8 is not provided with the protruding portion 8b, the hole 4a is provided only to the end surface 4x of the fixed shaft 4, and then, the end surface 4y is connected directly to the end surface 8x of the fixed body 8. In addition, when the fixed body 8 is provided with the protruding portion 8b and the fixed body 3 is not provided with the protruding portion 3b, the hole 4b is provided to the end surface 4y of the fixed shaft 4, and then, the end surface 4x is connected directly to the end surface 3x of the fixed body 3.

[Second Embodiment]

Figure 2:
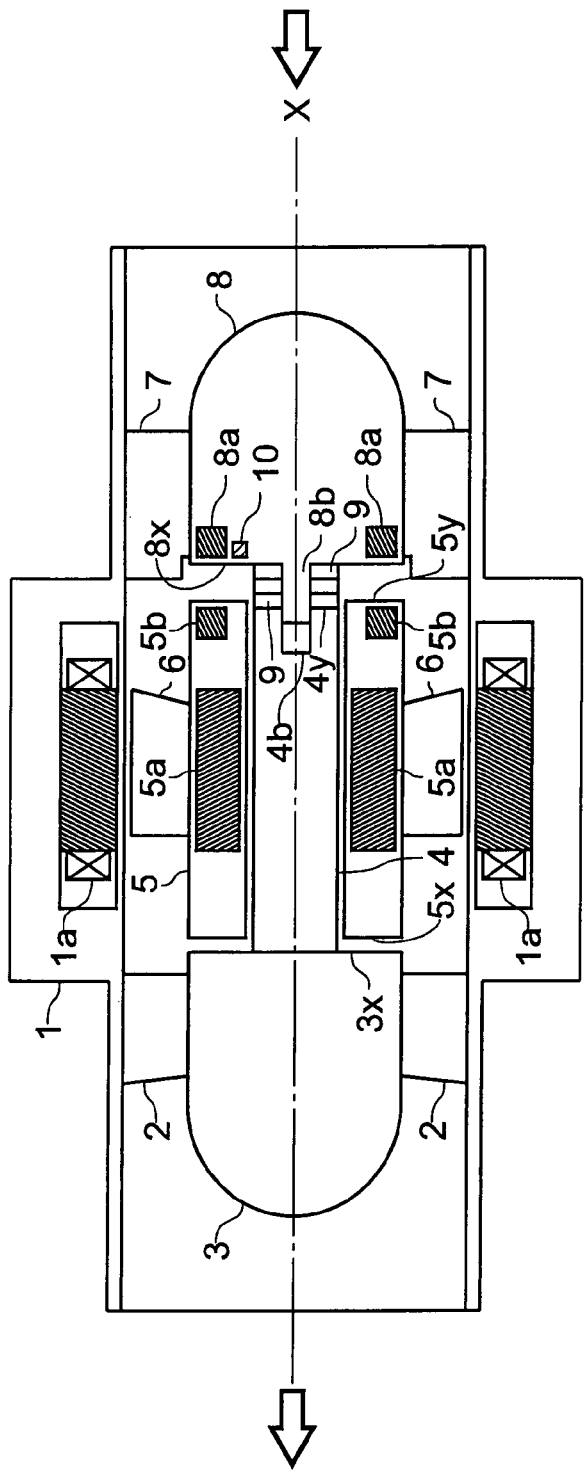
FIG. 2 is a cross-sectional view showing a construction of an artificial heart pump in accordance with a second embodiment of the present invention.

Referring to the drawings, a second embodiment of the present invention will be described hereinafter. FIG. 2 is a cross-sectional view showing a construction of an artificial heart pump in accordance with the present embodiment. In FIG. 2, same portions as in FIG. 1 will be provided with same symbols and the detailed description thereof will be omitted.

An artificial heart pump in FIG. 2 has a same construction as the artificial heart pump in FIG. 1, wherein permanent magnets 5c and 3a are excluded; and the construction that can be adjusted by the adjustment rings 9 is only provided in the part of the fixed body 8. To be specific, by having the clearances between the fixed bodies 3 and 8 and the sleeve 5 adjusted by the quantity and the thickness of the adjustment rings 9 that are installed circumferentially around the protruding portion 8b being provided to the fixed body 8, the magnetic forces of repulsion of the permanent magnets 5b and 8a are adjusted so as to balance the hydro thrust load, in order that the permanent magnets 5b and 8a function as thrust bearings under the operation conditions being applied.

In the artificial heart pump as described hereinabove, the housing 1 is connected to the outside periphery of the diffuser 2 and the fixed body 2 is connected to the inside periphery of the diffuser 2, so that the fixed body 2 is secured to the housing 1; the fixed shaft 4 is connected to the fixed body 2, so that the fixed shaft 4 is secured to the housing 1 by way of the fixed body 2. Then, the fixed body 8 having the adjustment rings 9 installed circumferentially around the protruding portion 8b is connected to the fixed shaft 4 in a manner that the protruding portion 8b is inserted into the hole 4b of the fixed shaft 4. By having the adjustment rings 9 installed between the fixed shaft 4 and the fixed body 8 as described hereinabove, the distance between the fixed bodies 3 and 8 is adjusted, thereby adjusting the clearances between the fixed bodies 3 and 8 and the sleeve 5 in order that the fixed bodies 3 and 8 do not contact the sleeve 5 under operation conditions to be applied.

The present embodiment is constructed in a manner that the fixed body 8 being equipped with a permanent magnet 8a and functioning as a thrust bearing is made adjustable, but may be constructed in a manner that the fixed body 3 having no permanent magnets is made adjustable. To be specific, by having a protruding portion 3b installed to the fixed body 3 and having a hole 4a provided to the end surface 4x of the fixed shaft 4, the clearances between the fixed bodies 3 and 8 and the sleeve 5 may be adjusted by the adjustment rings 9 being installed circumferentially around the protruding portion 3b.

[Third Embodiment]

Figure 3:
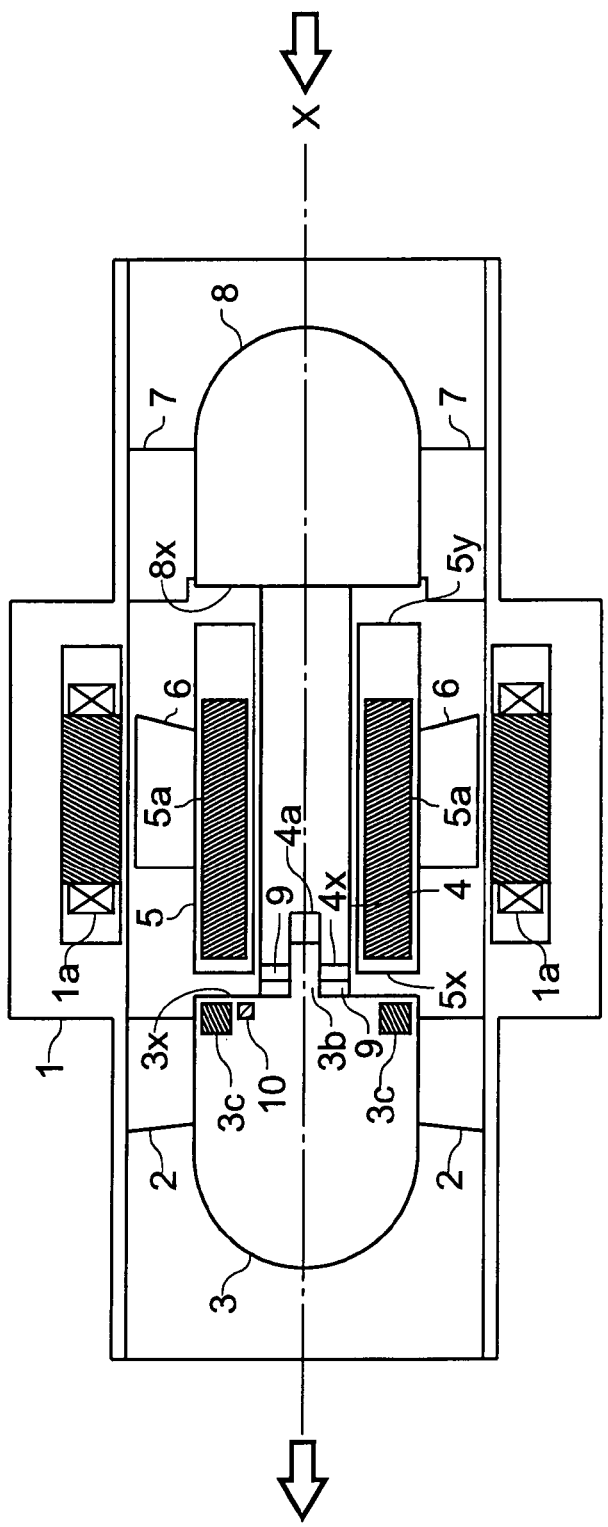
FIG. 3 is a cross-sectional view showing a construction of an artificial heart pump in accordance with a third embodiment of the present invention.

By referring to the drawings, a third embodiment of the present invention will be described hereinafter. FIG. 3 is a cross-sectional view showing a construction of an artificial heart pump in accordance with the present embodiment. In FIG. 3, same portions as in FIG. 1 will be provided with same symbols and the detailed description thereof will be omitted.

The artificial heart pump in FIG. 3 has a magnetic body 3c installed to the position where the permanent magnet 3a is installed, instead of having the permanent magnets 3a, 5b, 5c and 8a installed in the artificial heart pump that is constructed as shown in FIG. 1; utilizes the suction powers of the magnetic body 3c and the multi-pole oriented anisotropic permanent magnet 5a as the function of the thrust bearings; and has only the fixed body 3 constructed in a manner that adjustment by using the adjustment rings 9 is possible. To be specific, by adjusting the clearances between the fixed bodies 3 and 8 and the sleeve 5 by the quantity and the thickness of the adjustment rings 9 that are installed circumferentially around the protruding portion 3b being provided to the fixed body 3, the suction forces of the magnetic body 3c and the multi-pole oriented anisotropic permanent magnet 5a are adjusted so as to balance the hydro thrust loads in order that the magnetic body 3c and the multi-pole oriented anisotropic permanent magnet 5a may function as the thrust bearings.

In the artificial heart pump being constructed as described hereinabove, the fixed shaft 4 is fixed to the housing 1 by way of the fixed body 8, by having the fixed shaft 4 connected to the fixed body 8, which is fixed to the housing 1 by being connected to the inside peripheries of the current plates 7 having the outside peripheries thereof connected to the housing 1. Then, the fixed body 3 having the adjustment rings 9 installed circumferentially around the protruding portion 3b is connected to the fixed shaft 4 in a manner that the protruding portion 3b is inserted into the hole 4a of the fixed shaft 4. By installing the adjustment rings 9 between the fixed shaft 4 and the fixed body 8 so as to adjust the distance between the fixed bodies 3 and 8, the clearances between the fixed bodies 3 and 8 and the sleeve 5 are adjusted in order that the fixed bodies 3 and 8 will not contact the sleeve 5 under the operation conditions to be applied.

In addition, in accordance with the present embodiment, the fixed body 3 being provided with the magnetic body 3c which functions as a thrust bearing is adjustable, but the fixed body 8 having no magnetic bodies may be adjustable. To be specific, by providing a protruding portion 8b to the fixed body 8 and providing a hole 4b to the end surface 4y of the fixed shaft 4, the clearances between the fixed bodies 3 and 8 and the sleeve 5 may be adjusted by using the adjustment rings 9 being installed circumferentially around the protruding portion 8b.

Additionally, in accordance with the first through the third embodiments, both the diffuser 2 and the current plates 7 have the inside peripheries thereof connected to the outside wall surfaces of the fixed bodies 3 and 8 and have the outside peripheries thereof connected to the inside wall surface of the housing 1. However, either the diffuser 2 or the current plates 7 may be fixed by having either the inside peripheries thereof or the outside peripheries thereof connected.

Figure 4A:
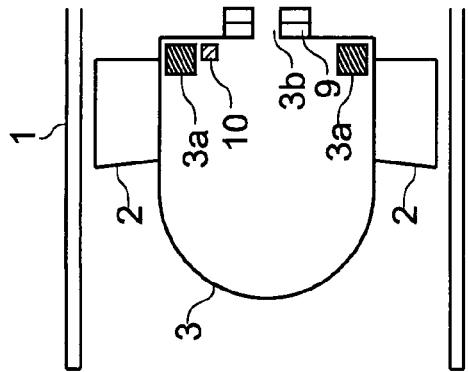
FIG. 4A is a view showing another construction of a current plate and a diffuser of an artificial heart pump in accordance with the first through the third embodiments.
Figure 4B:
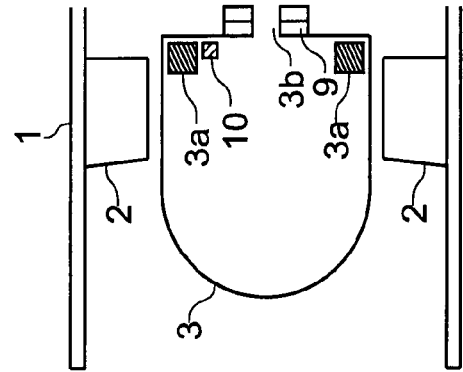
FIG. 4B is a view showing another construction of a current plate and a diffuser of an artificial heart pump in accordance with the first through the third embodiments.

To be specific, in accordance with the first or the second embodiment, as shown in FIG. 4A, the inside peripheries of the current plates 7 may be connected to the fixed body 8 so as to be fixed, while the outside peripheries of the current plates 7 may be separated. Or, as in FIG. 4B, the outside peripheries of the current plates 7 may be connected to the housing 1 so as to be fixed, while the inside peripheries of the current plates 7 may be separated. As a result, compared with a case in which both inside peripheries and the outside peripheries of the current plates 7 are connected, the fixed body 8 can be separated easily, thereby making the adjustment by using the adjustment rings 9 easy.

Figure 4C:
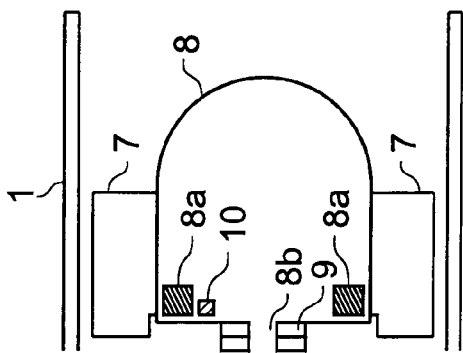
FIG. 4C is a view showing another construction of a current plate and a diffuser of an artificial heart pump in accordance with the first through the third embodiments.
Figure 4D:
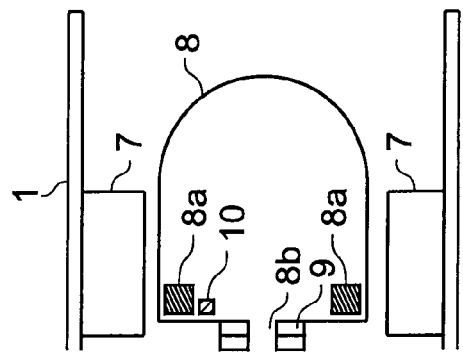
FIG. 4D is a view showing another construction of a current plate and a diffuser of an artificial heart pump in accordance with the first through the third embodiments.

Moreover, in accordance with the first or the third embodiment, as shown in FIG. 4C, the inside periphery of the diffuser 2 may be connected to the fixed body 3 so as to be fixed, while the outside periphery of the diffuser 2 may be separated; and as shown in FIG. 4D, the outside periphery of the diffuser 2 may be connected to the housing 1 so as to be fixed, while the inside periphery of the diffuser 2 may be separated. As a result, compared with a case in which both the inside periphery and the outside periphery of the diffuser 2 are connected, the fixed body 3 can be separated easily, thereby making the adjustment by using the adjustment rings 9 easy.

Figure 5B:
FIG. 5B is a view showing another construction of a fixed body and a fixed shaft of an artificial heart pump in accordance with the first through the third embodiments.
Figure 5B:
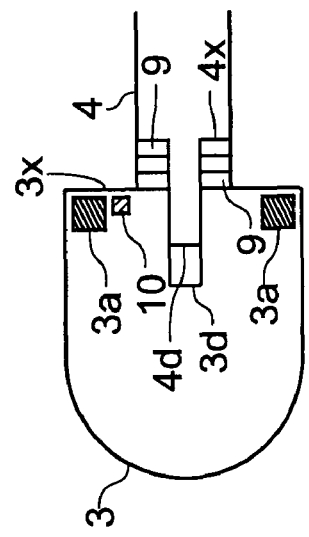
Figure 5A:
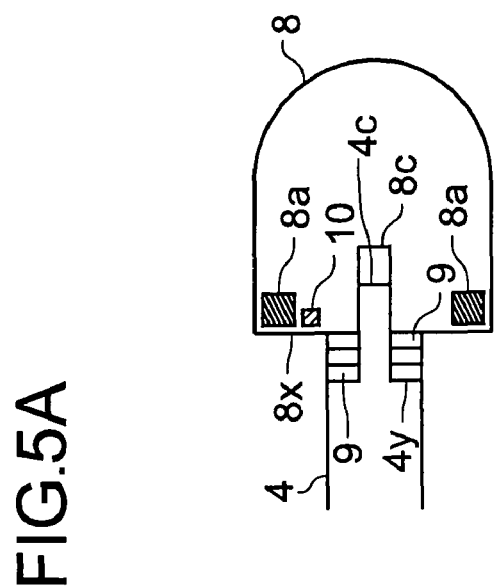
FIG. 5A is a view showing another construction of a fixed body and a fixed shaft of an artificial heart pump in accordance with the first through the third embodiments.

Furthermore, in accordance with the first or the second embodiment, by providing the protruding portion 8b to the fixed body 8 and inserting the protruding portion 8b into the hole 4a of the fixed shaft 4, the fixed body 8 is fixed. However, as shown in FIG. 5A, the protruding portion 4c may be provided to the center of the fixed body 8 side end surface 4y of the fixed shaft 4, while the hole 8c into which the protruding portion 4c is inserted may be provided to the center of the posterior end surface 8x of the fixed body 8. Hereat, the protruding portion 4c around which the adjustment rings 9 are installed circumferentially is inserted into the hole 8c. In the same manner as has been described, in accordance with the first or the third embodiment, as shown in 5B, the protruding portion 4d may be provided to the center of the fixed body 3 side end surface 4x of the fixed shaft 4, while the hole 3d into which the protruding portion 4d is inserted may be provided to the center of the anterior end surface 3x of the fixed body 3. Hereat, the protruding portion 4d around which the adjustment rings 9 are installed circumferentially is inserted into the hole 3d.

[Fourth Embodiment]

Figure 6:
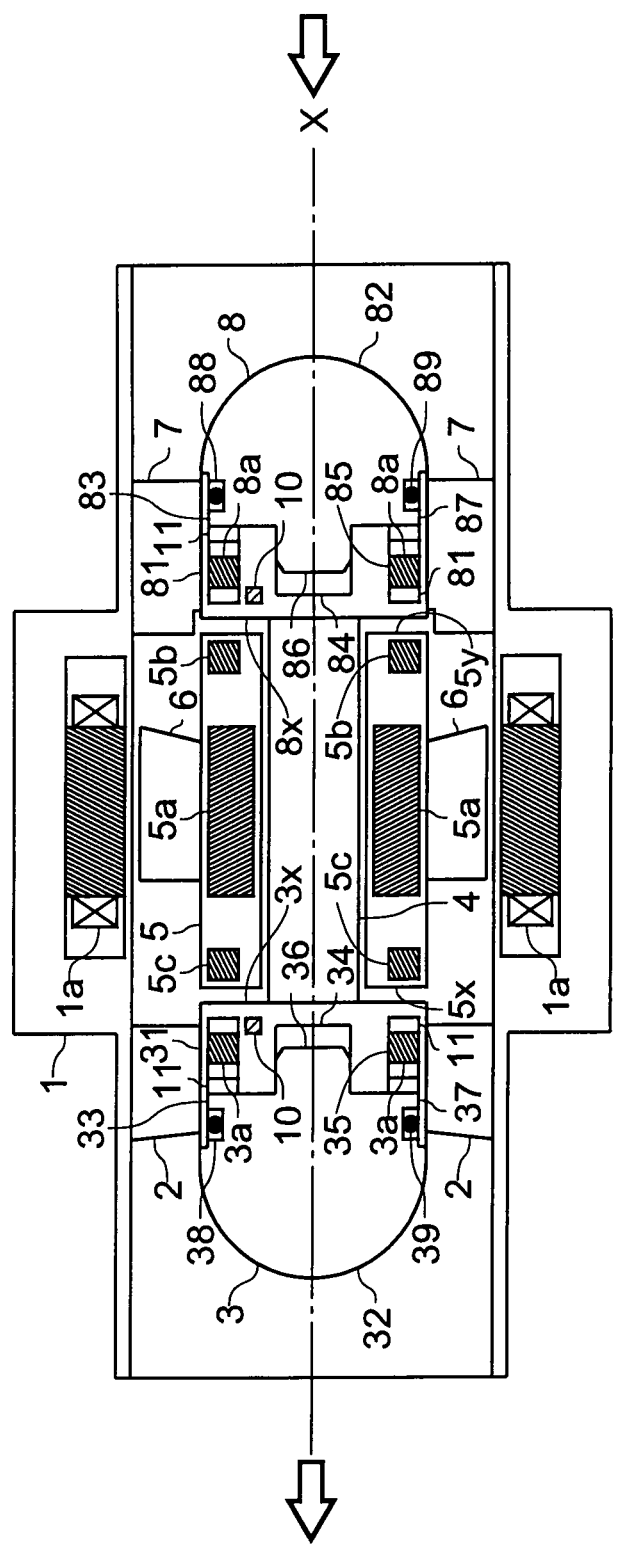
FIG. 6 is a cross-sectional view showing a construction of an artificial heart pump in accordance with a fourth embodiment of the present invention.

Referring to the drawings, a fourth embodiment of the present invention will be described hereinafter. FIG. 6 is a cross-sectional view showing a construction of an artificial heart pump in accordance with the present embodiment. In FIG. 6, same portions as in FIG. 1 will be provided with same symbols and the detailed description thereof will be omitted.

Being different from the artificial heart pump in FIG. 1, an artificial heart pump in FIG. 6 has each of the fixed bodies 3 and 8 constructed so as to be separated into a plurality of components, and at the same time, spacers 11 are used, which determine the positions to install the permanent magnets 3a and 8a to the fixed bodies 3 and 8, respectively, instead of having the adjustment rings 9 installed between the fixed bodies 3 and 8 and the fixed shaft 4. In the artificial heart pump described hereinabove, the fixed body 3 comprises a fixed-body component 31 which has a diffuser installed to the outside circumferential surface thereof; and a discharge cone 32 which is inserted into the fixed-body component 31 and has the posterior tip portion thereof elevated; and then, the fixed body 8 comprises a fixed-body component 81 which has the current plates 7 installed to the outside circumferential surface thereof; and a suction cone 82 which is inserted into the fixed-body component 81 and has the anterior tip portion thereof elevated.

Then, the fixed-body component 31 has the interior thereof ground off in a staircase pattern from the posterior end surface thereof toward the anterior end surface thereof. To be specific, a hole 33 having a large inside diameter is formed on the posterior end surface, and at the same time, a hole 34 having a smaller inside diameter than the hole 33 is formed on the bottom surface of the hole 33. In addition, the bottom surface of the hole 33 has a ring-shaped slot 35 formed around the hole 34, a spacer 11 and the permanent magnet 3a are inserted and installed into the ring-shaped slot 35. Moreover, a gap sensor 10 is installed to the clearance between the bottom surface of the hole 34 and the anterior end surface 3x of the fixed-body component 31.

Moreover, the discharge cone 32 has a protruding portion 36 being inserted into the hole 34 formed, and at the same time, the posterior side thereof from the protruding portion 36 is provided with a cylindrical portion 37 which is inserted into the hole 33 and has the outside diameter being approximately same as the inside diameter of the hole 33; a ring-shaped slot 38 being formed on a part of the outside wall surface of the cylindrical portion 37; and an O-ring 39 consisting of an elastic body and being fit into the ring-shaped slot 38. Then, the hole 34 of the fixed-body component 31 and the protruding portion 36 of the discharge cone 32 are threaded, respectively, and then, the fixed-body component 31 has the discharge cone 32 installed thereto by having the protruding portion 36 rotated and inserted into the hole 34.

In the same manner as described hereinabove, the fixed-body component 81 is constructed in a staircase pattern from the anterior end surface thereof toward the posterior end surface thereof, having a hole 83 having a large inside diameter and a hole 84 having a small inside diameter formed therein, and at the same time, having a ring-shaped slot 85 formed around the hole 84 on the bottom surface of the hole 83. Then, a spacer 11 and a permanent magnet 8a are inserted into the slot 85, and a gap sensor 10 is installed between the bottom surface of the hole 84 and the posterior end surface 8x of the fixed body 81. In addition, the suction cone 82 is provided with a protruding portion 86 and a cylindrical portion 87 being inserted into the holes 84 and 83, respectively; a slot 88 being formed on a part of the outside wall surface of the cylindrical portion 87; and an O-ring 89 being fit into the slot 88. Then, the hole 84 of the fixed-body component 81 and the protruding portion 86 of the suction cone 82 are threaded, respectively, and then, the fixed-body component 81 has the suction cone 82 installed thereto by having the protruding portion 86 rotated and inserted into the hole 84.

When the fixed bodies 3 and 8 are formed as described hereinabove, a plurality of spacers 11 and the permanent magnets 3a and 8a are inserted into the slots 35 and 85 of the fixed-body components 31 and 81, respectively, after the fixed-body components are connected to the rotating shaft 4 around which a sleeve 5 is installed circumferentially. Hereat, the depth of the slot 35 in the axial direction of the central axis X is equal to the total of the lengths in the axial direction of the central axis X of a plurality of the spacers 11 and the permanent magnet 3a being inserted into the slot 35, respectively. In addition, the depth of the slot 85 in the axial direction of the central axis X is equal to the total of the lengths in the axial direction of the central axis X of a plurality of the spacers 11 and the permanent magnet 8a being inserted into the slot 85, respectively.

Then, the protruding portion 36 of the discharge cone 32 is inserted into the hole 34 of the fixed-body component 31 having the spacers 11 and the permanent magnet 31 installed, so as to be fit to the threaded slots of each other, and as a result, the discharge cone 32 is fixed to the fixed-body component 31. In the same manner as has been described, the protruding portion 86 of the suction cone 82 is inserted into the hole 84 of the fixed-body component 81 having the spacers 11 and the permanent magnet 8a installed, so as to be fit to the threaded slots of each other, and as a result, the suction cone 82 is fixed to the fixed-body component 81. Hereat, the clearance between the inside wall surface of the fixed-body component 31 and the outside wall surface of the discharge cone 32 is sealed by the O-ring 39 being installed to the slot 38 of the cylindrical portion 37 of the discharge cone 32, and at the same time, the clearance between the inside wall surface of the fixed-body component 81 and the outside wall surface of the suction cone 82 is sealed by the O-ring 89 being installed to the slot 88 of the cylindrical portion 87 of the suction cone 82. In consequence, the bloods are prevented from flowing into the interiors of the fixed bodies 3 and 8.

Being constructed as described hereinabove, the distance between the permanent magnets 3a and 5c is specified by the quantity of the spacers 11 being installed to the anterior portion before the permanent magnet 3a, thereby determining the magnetic forces of repulsion of the permanent magnets 3a and 5c. At the same time, the distance between the permanent magnets 8a and 5b is specified by the quantity of the spacers 11 being installed to the posterior portion after the permanent magnet 8a, thereby determining the magnetic forces of repulsion of the permanent magnets 8a and 5b.

In consequence, same as the first embodiment, when the artificial heart pump is constructed as described hereinabove during the manufacturing process, commissioning (trial operation) is performed, and the clearances between the fixed bodies 3 and 8 and the sleeve 5 are measured with the gap sensors 10 during startup and shutdown of the sleeve 5 and under the condition that the hydro thrust load is small. Then, in order to optimize the clearances between the fixed bodies 3 and 8 and the sleeve 5, the quantity of the spacers 11 to be installed before the permanent magnet 3a is specified for the fixed body 3, and the quantity of the spacers 11 to be installed after the permanent magnet 8a is specified for the fixed body 8, respectively, thereby determining the locations to install the permanent magnets 3a and 8a. When the locations to install the permanent magnets 3a and 8a are determined in such a manner as described hereinabove, the gap sensors 10 will be removed from the fixed-body components 31 and 81, respectively, and subsequently, the discharge cone 32 and the suction cone 82 will be re-installed to the fixed-body components 31 and 81. In addition, during the manufacturing process, instead of by installing O-rings 39 and 89, the interiors of the fixed bodies 3 and 8 are sealed by welding the space by the slot 38 of the discharge cone 32 and the inside wall surface of the fixed-body component 31 as well as by welding the space by the slot 88 of the suction cone 82 and the inside wall surface of the fixed-body component 81.

In accordance with the present embodiment, a gap sensor 10 is installed to each of the fixed-body components 31 and 81, respectively. However, a gap sensor 10 may be installed to only one of the fixed-body components 31 and 81. To be specific, when a gap sensor 10 is installed inside the fixed-body component 31, the clearance between the fixed body 3 and the sleeve 5 is measured with the gap sensor 10. Then, the clearance between the fixed body 8 and the sleeve 5 is obtained from the measured clearance between the fixed body 3 and the sleeve 5 and the axial lengths of the fixed shaft 4 and the sleeve 5. In addition, the clearances of an appropriate dimension between the fixed bodies 3 and 8 and the sleeve 5 may not be measured with the gap sensors 10 but may be by externally measuring the contact of the fixed bodies 3 and 8 with the sleeve 5.

As mentioned hereinabove, in accordance with the present embodiment, each location to install the permanent magnets 3a and 8a, respectively, can easily be adjusted with the spacers 11, and the thrust forces being applied by the permanent magnets 3a, 8a, 5b and 5c can easily be adjusted. Additionally, being different from the first embodiment, in accordance with the present embodiment, in order to change the locations to install the permanent magnets 3a and 8a inside the fixed bodies 3 and 8, the thrust forces can be adjusted, keeping the distance between the anterior end surface 3x of the fixed body 3 and the posterior end surface 8x of the fixed body 8 constant.

Figure 7:
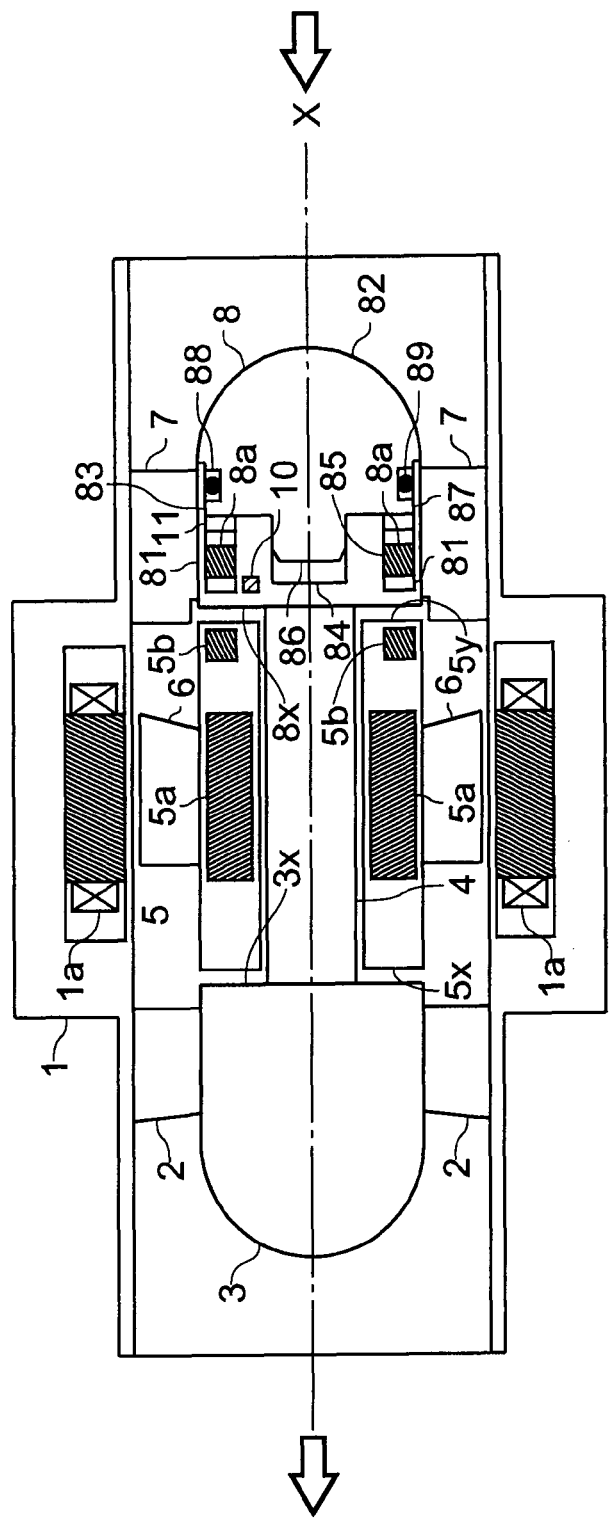
FIG. 7 is a cross-sectional view showing another construction of an artificial heart pump in accordance with the fourth embodiment of the present invention.
Figure 8:
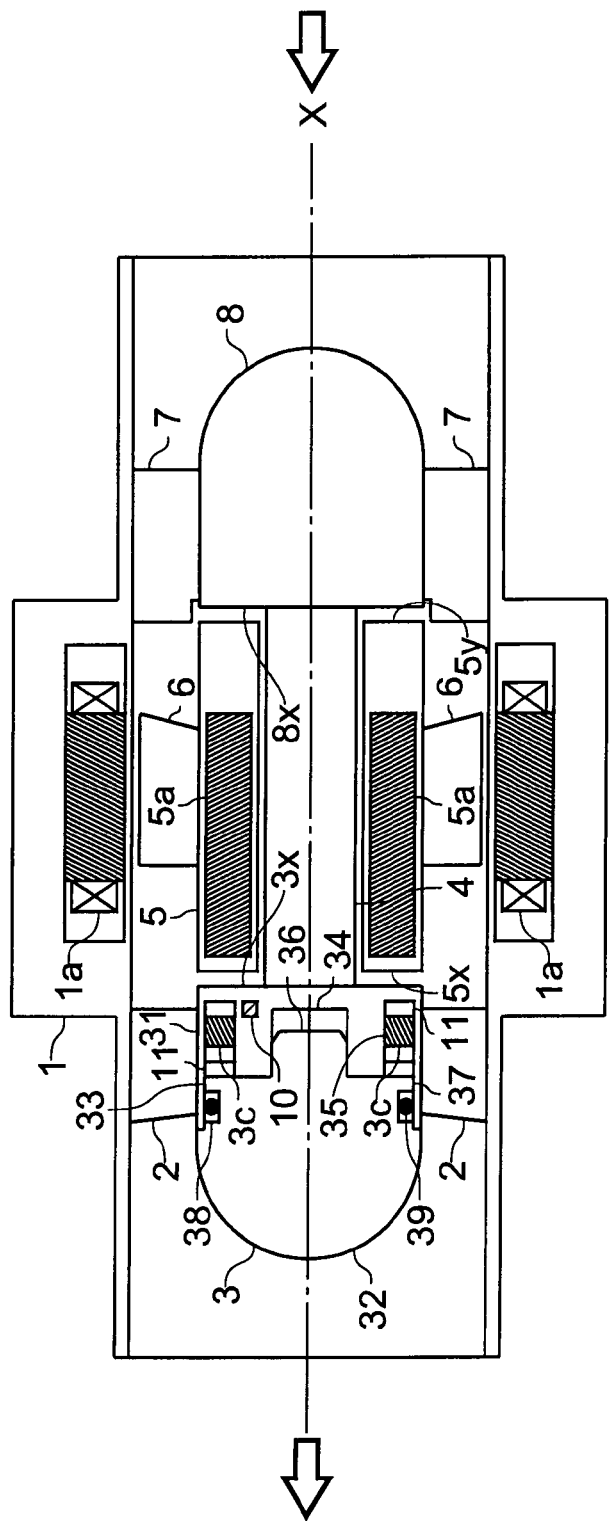
FIG. 8 is a cross-sectional view showing another construction of an artificial heart pump in accordance with the fourth embodiment of the present invention.

Moreover, in accordance with the present embodiment, the permanent magnets 3a, 8a, 5b and 5c are provided, and the positions of the permanent magnets 3a and 8a can be adjusted in both fixed bodies 3 and 8. However, the positions of the permanent magnets 3a and 8a may be adjusted only in one of the fixed bodies 3 and 8. In addition, same as the second embodiment, as shown in FIG. 7, the artificial heart pump may have same construction as the construction of the artificial heart pump in FIG. 6 from which the permanent magnets 5c and 3a are excluded, and may be made adjustable with the spacers 11 for the fixed body 8 only. Furthermore, same as the third embodiment, as shown in FIG. 8, the magnetic body 3c may be provided instead of the permanent magnets 3a, 8a, 5b and 5c in the construction of the artificial heart pump in FIG. 6, and only the fixed body 3 may be made adjustable with the spacers 11, so that the position of the magnetic body 3c may be adjusted.

[Fifth Embodiment]

Figure 9:
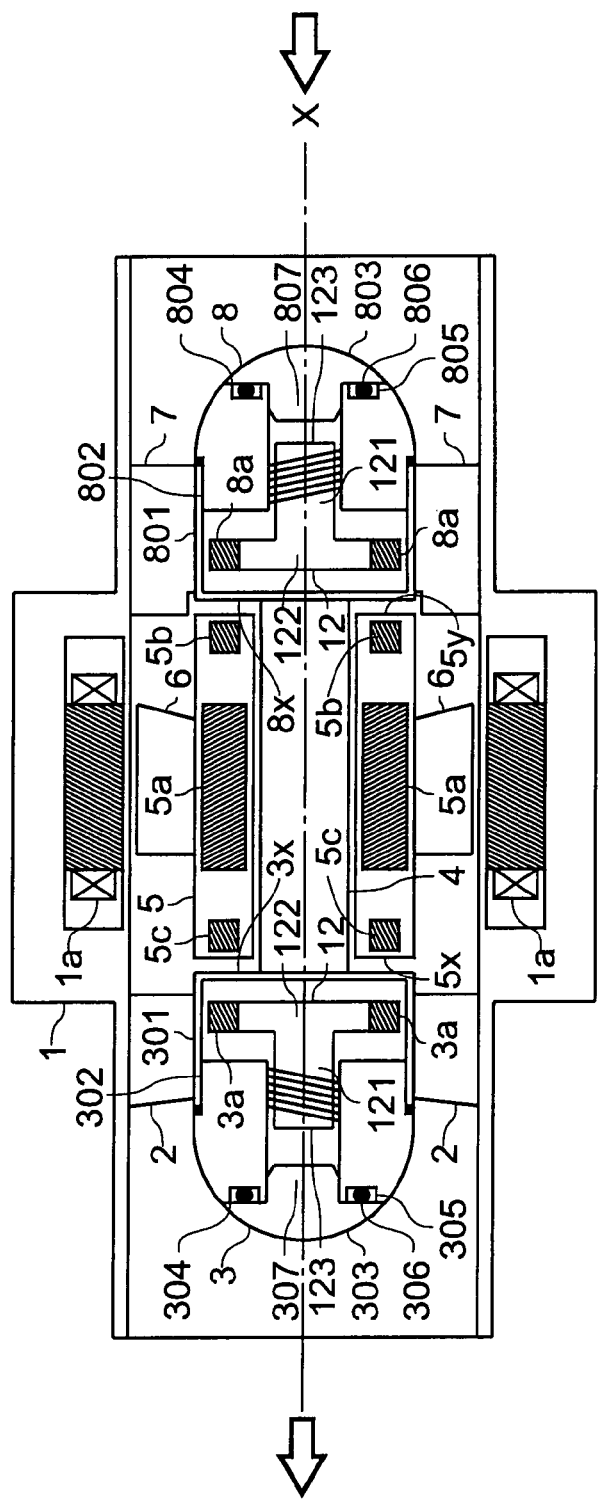
FIG. 9 is a cross-sectional view showing a construction of an artificial heart pump in accordance with a fifth embodiment of the present invention.

Referring to the drawings, a fifth embodiment of the present invention will be described hereinafter. FIG. 9 is a cross-sectional view showing a construction of an artificial heart pump in accordance with the present embodiment. In FIG. 9, same portions as in FIG. 6 will be provided with same symbols and the detailed description thereof will be omitted.

The artificial heart pump in FIG. 9 is different from the artificial heart pump in FIG. 6 in the construction of the fixed bodies 3 and 8; wherein, the locations to install the permanent magnets 3a and 8a are not specified by the spacers 11 but the locations to install the permanent magnets 3a and 8a are specified by the adjustment member 12 having a threaded portion provided. In such an artificial heart pump as described hereinabove, the fixed body 3 comprises: a fixed-body component 301 having the posterior side thereof opened; a stationary portion of the discharge cone 302 being inserted into the opening on the posterior side of the fixed-body component 301; a tip portion of the discharge cone 303 being inserted into a hole being provided to the stationary portion of the discharge cone 302; and an adjustment member 12 being connected to the permanent magnet 3a. In addition, same as the fixed body 3, the fixed body 8 comprises: a fixed-body component 801 having the anterior side thereof opened; a stationary portion of the suction cone 802 being inserted into the opening of the fixed-body component 801; a tip portion of the suction cone 803 being inserted into a hole being provided to the stationary portion of the suction cone 802; and an adjustment member 12 being connected to the permanent magnet 8a.

Then, the fixed-body components 301 and 801 are cylindrically shaped; wherein, the fixed-body component 301 has a bottom surface on the anterior side thereof, while the fixed-body component 801 has a bottom surface on the posterior side thereof. In addition, the stationary portion of the discharge cone 302 being inserted into the opening on the posterior side of the fixed-body component 310 has the anterior side thereof shaped in a staircase pattern, wherein the outside diameter of a portion being inserted into the opening of the fixed-body component 301 is approximately equal to the inside diameter of the opening of the fixed-body component 301, and the outside diameter of the portion which is not inserted into the opening of the fixed-body component 301 is equal to the outside diameter of the fixed-body component 301. The stationary portion of the discharge cone 302 is connected to the fixed-body component 301 so as to be integrated, by being welded at a portion thereof which comes to contact with the end surface of the opening of the fixed-body component 301.

Moreover, the stationary portion of the discharge cone 302 has the posterior side thereof constructed to be curved toward the center and has a flat end surface 304 formed in the neighborhood of the center so as to come to contact with the anterior side end surface of the tip portion of the discharge cone 303. The stationary portion of the discharge cone 302 has a through hole formed in the axial direction of the central axis X; wherein, the tip portion of the discharge cone 303 is inserted from the posterior side of the hole and an adjustment member 12 is inserted from the anterior side of the hole. The tip portion of the discharge cone 303 has the posterior portion thereof curved toward the center and has the center portion thereof elevated; wherein, the anterior portion thereof is provided with a protruding portion 307 that protrudes, and the protruding portion 307 is inserted into the hole of the stationary portion of the discharge cone 302. Furthermore, the end surface 304 of the posterior portion of the stationary portion of the discharge cone 302 has a ring-shaped slot 305 provided, and by having an O-ring 306 of an elastic body fit into the slot 305, the contact surfaces of the tip portion of the discharge cone 303 and the stationary portion of the discharge cone 304 are sealed.

Same as the stationary portion of the discharge cone 302, the stationary portion of the suction cone 802 has the anterior side thereof constructed to be curved toward the center; has a flat end surface 804 formed in the neighborhood of the center; and in addition, has a through hole formed in the axial direction of the central axis X. Same as the tip portion of the discharge cone 303, the tip portion of the suction cone 803 has the posterior portion thereof provided with a protruding portion 807 that protrudes, and the protruding portion 807 is inserted into the hole of the stationary portion of the suction cone 802. Additionally, the end surface 804 of the stationary portion of the suction cone 802 has a ring-shaped slot 805 provided, and an O-ring 806 of an elastic body is fit into the slot 805.

The adjustment member 12 being inserted from the anterior hole of the stationary portion of the discharge cone 302 and from the posterior hole of the stationary portion of the suction cone 802 have two cylindrical structures 121 and 122 having different diameters overlapped in the direction of the central axis X; wherein, the diameter of the cylindrical structure 121 being inserted into the stationary portion of the discharge cone 302 and the stationary portion of the suction cone 802 is approximately equal to the inside diameter of the holes of the stationary portion of the discharge cone 302 and the stationary portion of the suction cone 802. In addition, the diameter of the cylindrical structure 122 being surrounded by the fixed-body components 301 and 801 is larger than the diameter of the cylindrical structure 121. Then, the permanent magnets 3a and 8a are installed to the adjustment member 12 in a manner that the inside circumferential surfaces of the permanent magnets 3a and 8a come to contact with the outside circumferential surface of the cylindrical structure 122.

Moreover, the holes of the stationary portion of the discharge cone 302 and the stationary portion of the suction cone 802, the protruding portions 307 and 807 of the tip portion of the discharge cone 303 and the tip portion of the suction cone 803, and the cylindrical structure 121 of the adjustment members 12 are thread cut, respectively. In consequence, by having the protruding portion 307 and the cylindrical stricture 121 rotated and inserted into the hole of the stationary portion of the discharge cone 302, the tip portion of the discharge cone 303 and the adjustment member 12 are fixed to the stationary portion of the discharge cone 302. Additionally, by having the protruding portion 807 and the cylindrical structure 121 rotated and inserted into the hole of the stationary portion of the suction cone 802, the tip portion of the suction cone 803 and the adjustment member 12 are fixed to the stationary portion of the suction cone 802.

When the fixed bodies 3 and 8 are constructed as described hereinabove, first, the fixed-body components 301 and 801 are connected to the rotating shaft 4 around which the sleeve 5 is installed circumferentially, and subsequently, the adjustment members 12 having the permanent magnets 3a and 8a installed are inserted into each of the holes of the stationary portion of the discharge cone 302 and the stationary portion of the suction cone 802, respectively. Then, the stationary portion of the discharge cone 302 and the stationary portion of the suction cone 802 are inserted into the openings of the fixed-body components 301 and 801, respectively, from the side where the adjustment members 12 are inserted, in a manner that the fixed-body components 301 and 801 cover the cylindrical structure 122 of the adjustment members 12. To be specific, the permanent magnet 3a is installed inside the enclosed space being constructed by the fixed-body component 301 and the stationary portion of the discharge cone 302, and the permanent magnet 8*a* is installed inside the enclosed space being constructed by the fixed-body component 801 and the stationary component of the suction cone 802.

When the stationary portion of the discharge cone 302 and the stationary portion of the suction cone 802 are inserted into the fixed-body components 301 and 801, respectively, and connected by welding, the protruding portions 307 and 807 of the tip portion of the discharge cone 303 and the tip portion of the suction cone 803, respectively, are inserted into the holes being provided to the end surfaces 304 and 804 of the stationary portion of the discharge cone 302 and the stationary portion of the suction cone 802, respectively. Then, commissioning is performed, and the clearances between the fixed bodies 3 and 8 and the sleeve 5 are measured under the operation condition that the hydro thrust load is small and during startup and shutdown.

When the artificial heart pump is manufactured as described hereinabove and the clearances between the fixed bodies 3 and 8 and the sleeve 6 are measured during commissioning, the locations to install the permanent magnets 3*a* and 8*a* are specified so as to optimize the dimensions of the measured clearances between the fixed bodies 3 and 8 and the sleeve 5. Hereat, each of the tip portion of the discharge cone 303 and the tip portion of the suction cone 803 is removed from the stationary portion of the discharge cone 302 and the stationary portion of the suction cone 802, respectively.

Then, the locations to install the permanent magnets 3*a* and 8*a* are specified by inserting a tool into the holes of the stationary portion of the discharge cone 302 and the stationary portion of the suction cone 802, respectively, rotating the adjustment members 12 with the tool and shifting the adjustment members 12 in the axial direction of the central axis X. The end surface 123 of the cylindrical structure 121 of the adjustment member 12 has such a slot formed as has the same shape as the shape of the tip of the tool, and then, the adjustment member 12 is rotated by inserting the tip of the tool into the slot.

In the manufacturing process, the locations to install the permanent magnets 3*a* and 8*a* is specified, then the adjustment member 12 and the inside wall surface of the hole of the stationary portion of the discharge cone 302 are fixed by welding or by using an adhesive material and the adjustment member 12 and the inside wall surface of the hole of the stationary portion of the suction cone 802 are fixed by welding or by using an adhesive material, so that thereby the adjustment member 12 is prevented from rotating and thus fixed. Subsequently, each of the tip portion of the discharge cone 303 and the tip portion of the suction cone 803 is inserted again into the stationary portion of the discharge cone 302 and the stationary portion of the suction cone 802, respectively. Hereat, instead of having the O-rings 306 and 806 installed, the interiors of the fixed bodies 3 and 8 are sealed by welding the space being made by the slot 305 of the stationary portion of the discharge cone 302 and the anterior-side surface of the tip portion of the discharge cone 303 and welding the space being made by the slot 805 of the stationary portion of the suction cone 802 and the posterior-side surface of the tip portion of the suction cone 803.

As described hereinabove, in accordance with the present embodiment, the locations to install the permanent magnets 3*a* and 8*a* can easily be adjusted by using a tool. In accordance with the present embodiment, same as the fourth embodiment, the gap sensor 10 may be installed to at least one of the fixed-body components 301 and 801 for measuring the clearances between the fixed bodies 3 and 8 and the sleeve 5 during commissioning. Additionally, the clearances between the fixed bodies 3 and 8 and the sleeve 5 may not be measured by the gap sensor 10 but may be measured by externally measuring the contact of the fixed bodies 3 and 8 with the sleeve 5.

Figure 10:
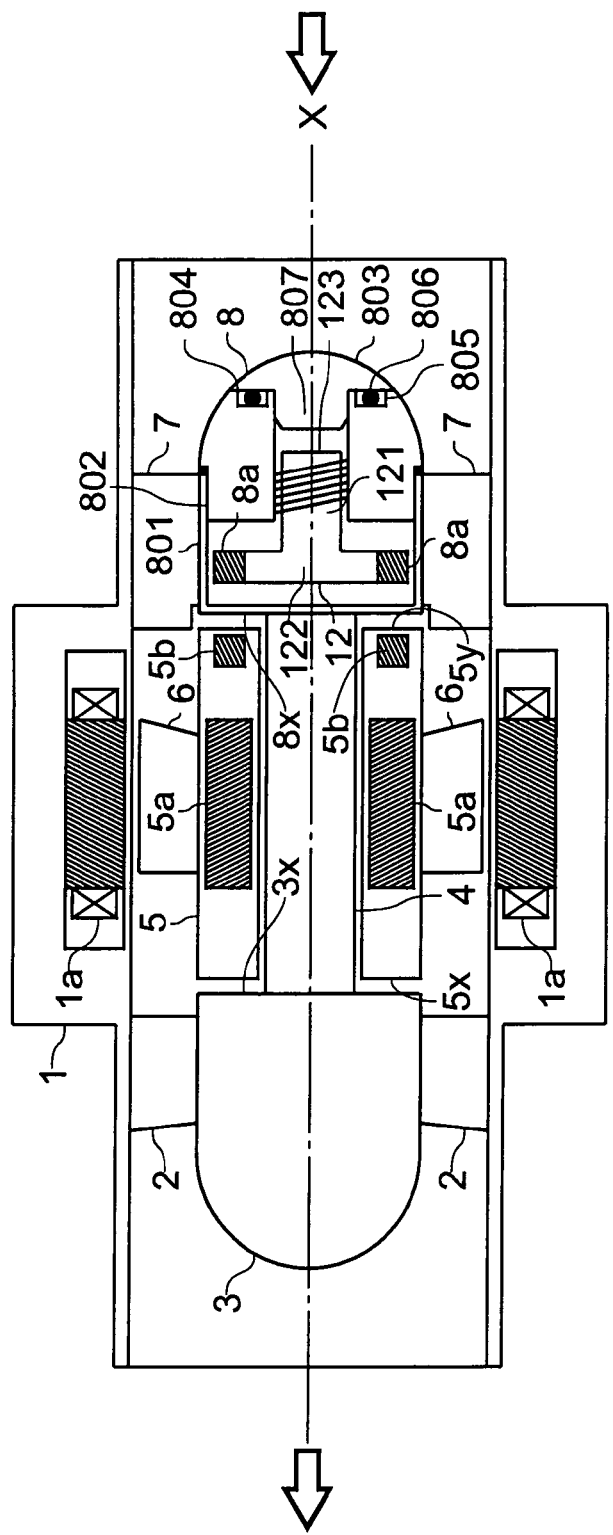
FIG. 10 is a cross-sectional view showing another construction of an artificial heart pump in accordance with the fifth embodiment of the present invention.
Figure 11:
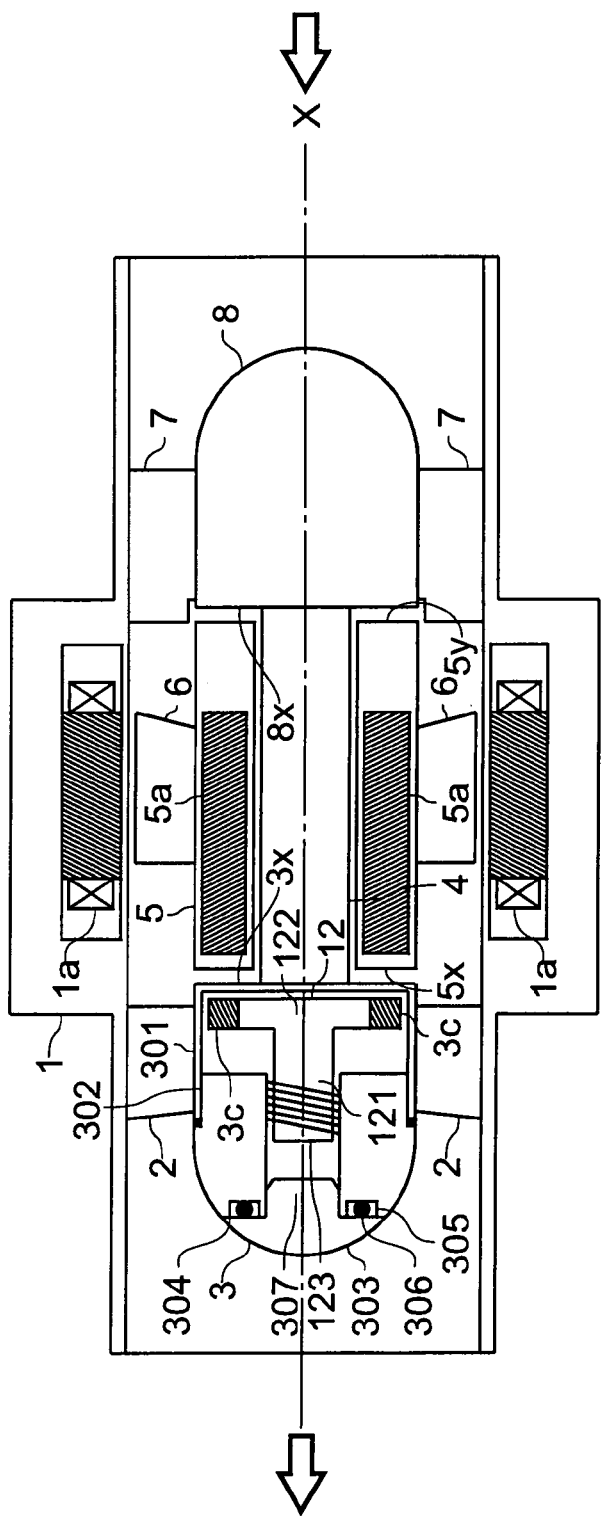
FIG. 11 is a cross-sectional view showing another construction of an artificial heart pump in accordance with the fifth embodiment of the present invention.

In accordance with the present embodiment, same as the fourth embodiment, the permanent magnets 3*a*, 8*a*, 5*b* and 5*c* are provided, and at the same time, the locations of the permanent magnets 3*a* and 8*a* can be adjusted by both fixed bodies 3 and 8. However, the locations of the permanent magnets 3*a* and 8*a* may be adjusted only by either of the fixed bodies 3 and 8. In addition, same as the second embodiment, as shown in FIG. 10, the artificial heart pump may have same construction as the construction of the artificial heart pump in FIG. 9 from which the permanent magnets 5*c* and 3*a* are excluded, and may be made adjustable with the adjustment member 12 for the fixed body 8 only. Furthermore, same as the third embodiment, as shown in FIG. 11, a magnetic body 3*c* may be provided instead of the permanent magnets 3*a*, 8*a*, 5*b* and 5*c* in the construction of the artificial heart pump in FIG. 9, and only the fixed body 3 may be made adjustable with the adjustment member 12, so that the position of the magnetic body 3*c* may be adjusted.

Moreover, same as the first embodiment, in accordance with the fourth and the fifth embodiments, the connection portions of the fixed bodies 3 and 8 to the fixed shaft 8 may have the protruding portions 3*b* and 8*b* provided to the fixed bodies 3 and 8 and have the holes 4*a* and 4*b* provided to the fixed shaft 4, and then, the protruding portions 3*b* and 8*b* of the fixed bodies 3 and 8 may have the adjustment rings 9 circumferentially installed, respectively. In addition, as shown in FIG. 5A and FIG. 5B, by having holes 3*d* and 8*c* provided to the fixed bodies 3 and 8 and having the protruding portions 4*c* and 4*d* to the fixed shaft 4, the protruding portions 4*c* and 4*d* of the fixed shaft 4 may have the adjustment rings 9 installed circumferentially. As a result, the distance between the fixed bodies 3 and 8 can be adjusted by using the adjustment rings 9.

Figure 12:
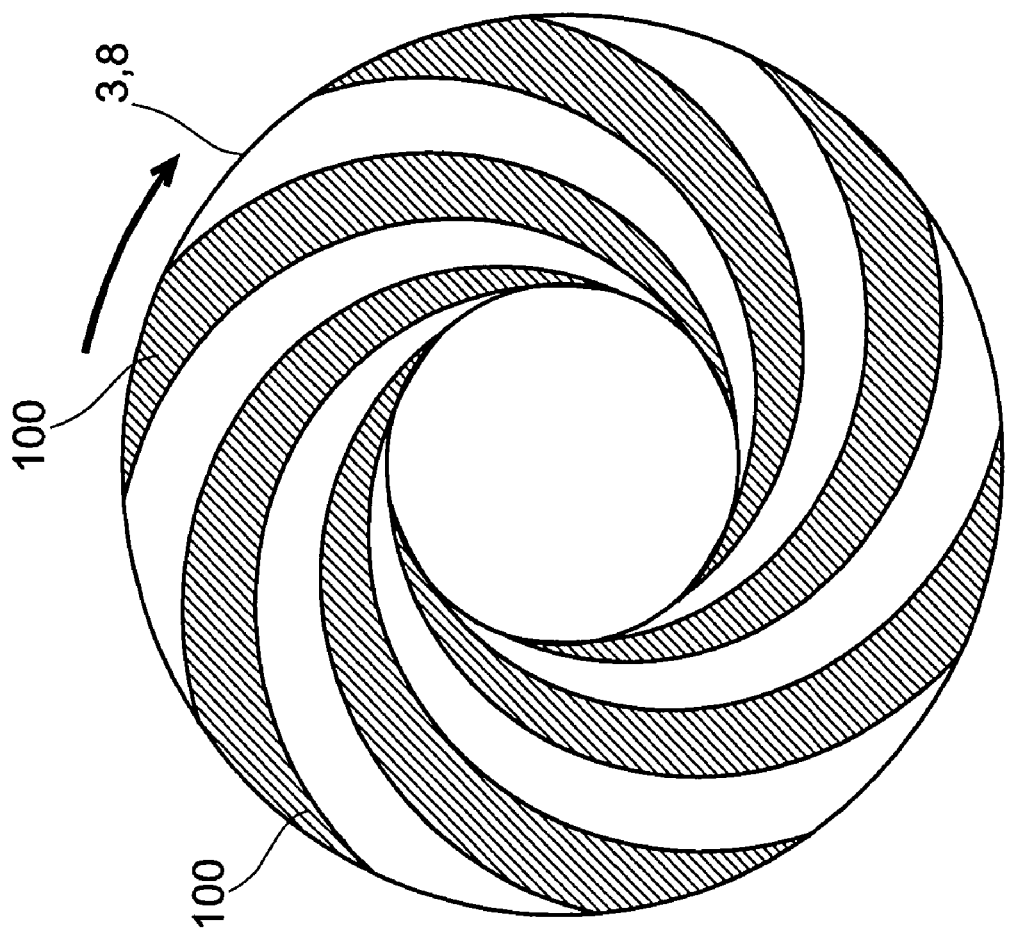
FIG. 12 is a view showing a construction of a thrust-hydrodynamic-pressure-generating groove.

Furthermore, as described in the Patent Literature No. 1, in accordance with the first through the fifth embodiments, each of the anterior end surface 3*x* of the fixed body 3 and the posterior end surface 8*x* of the fixed body 8 may have a plurality of spiral thrust-hydrodynamic-pressure-generating grooves 100 being shown in FIG. 12 formed. To be specific, thrust hydrodynamic pressures generated in the bloods flowing to the thrust-hydrodynamic-pressure-generating grooves 100 and the magnetic forces of repulsion being caused by the permanent magnets 3*a*, 5*b*, 5*c* and 8*a* support the thrust loads being applied to the sleeve 5.

Figure 13:
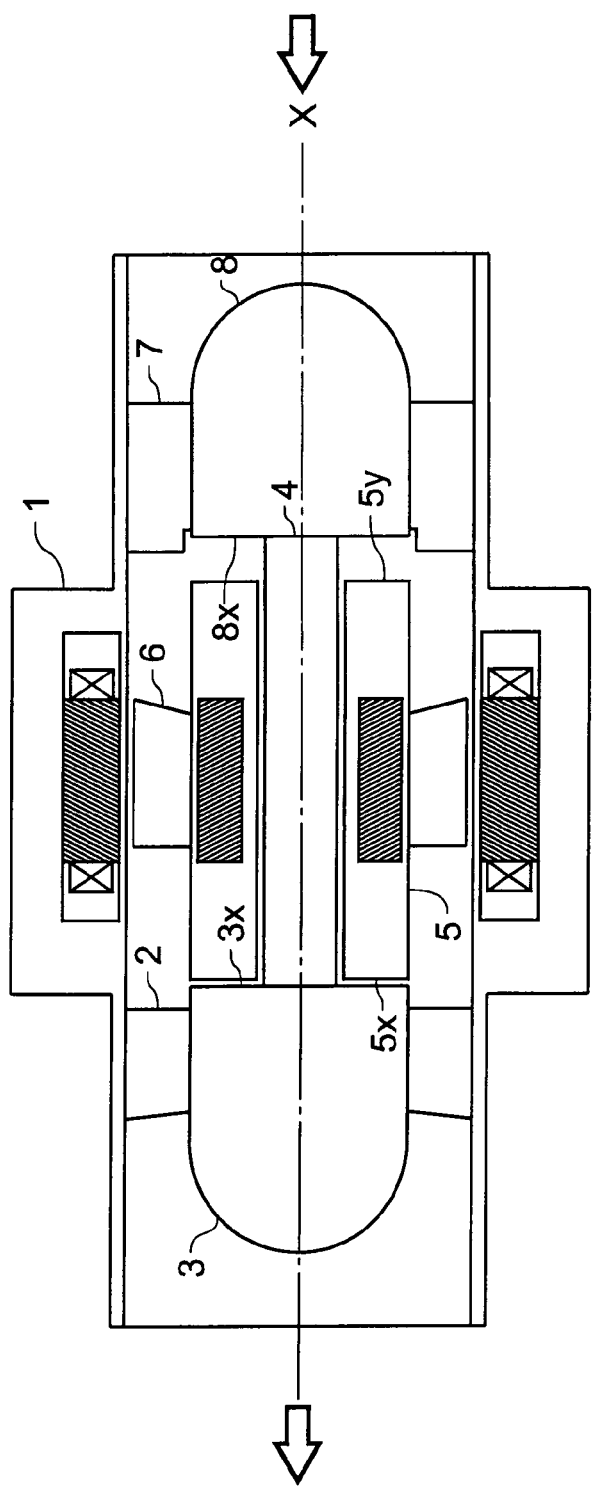
FIG. 13 is a view showing a construction of an artificial heart pump, wherein a thrust-hydrodynamic-pressure-generating groove is installed to the posterior-side fixed body.
Figure 14:
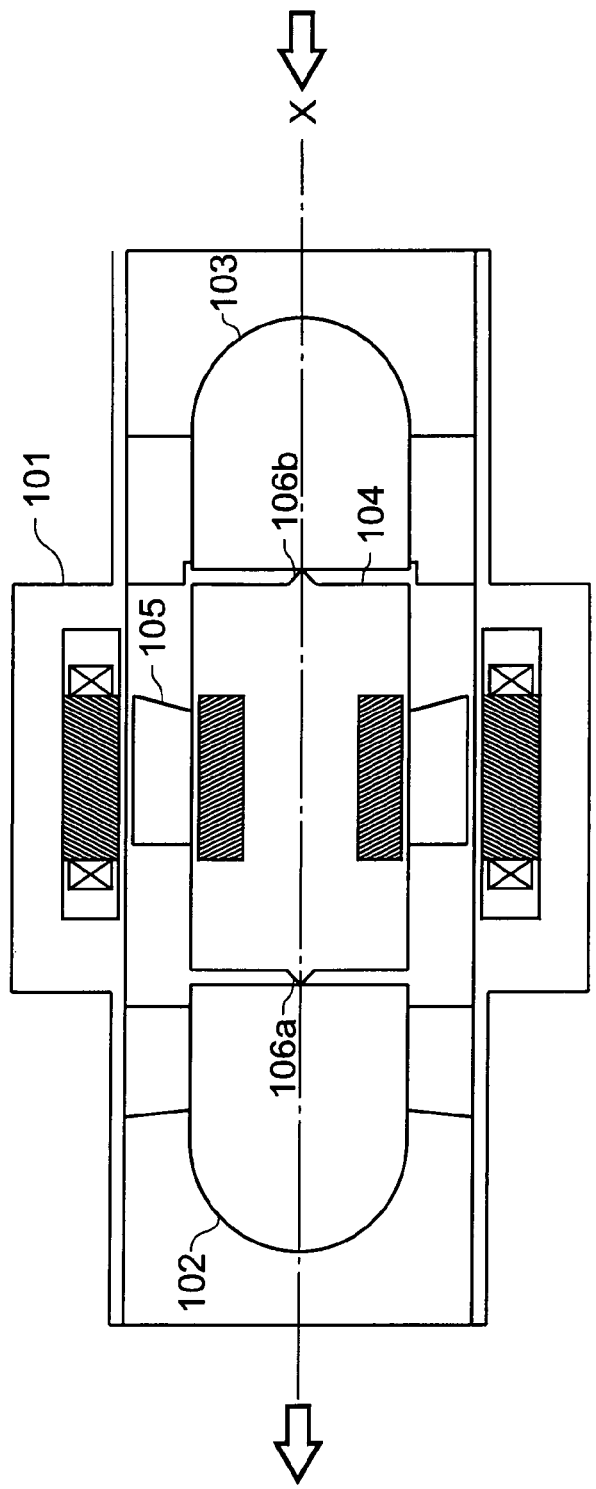
FIG. 14 is a cross-sectional view showing a construction of a conventional artificial heart pump employing pivot bearings.
Figure 15:
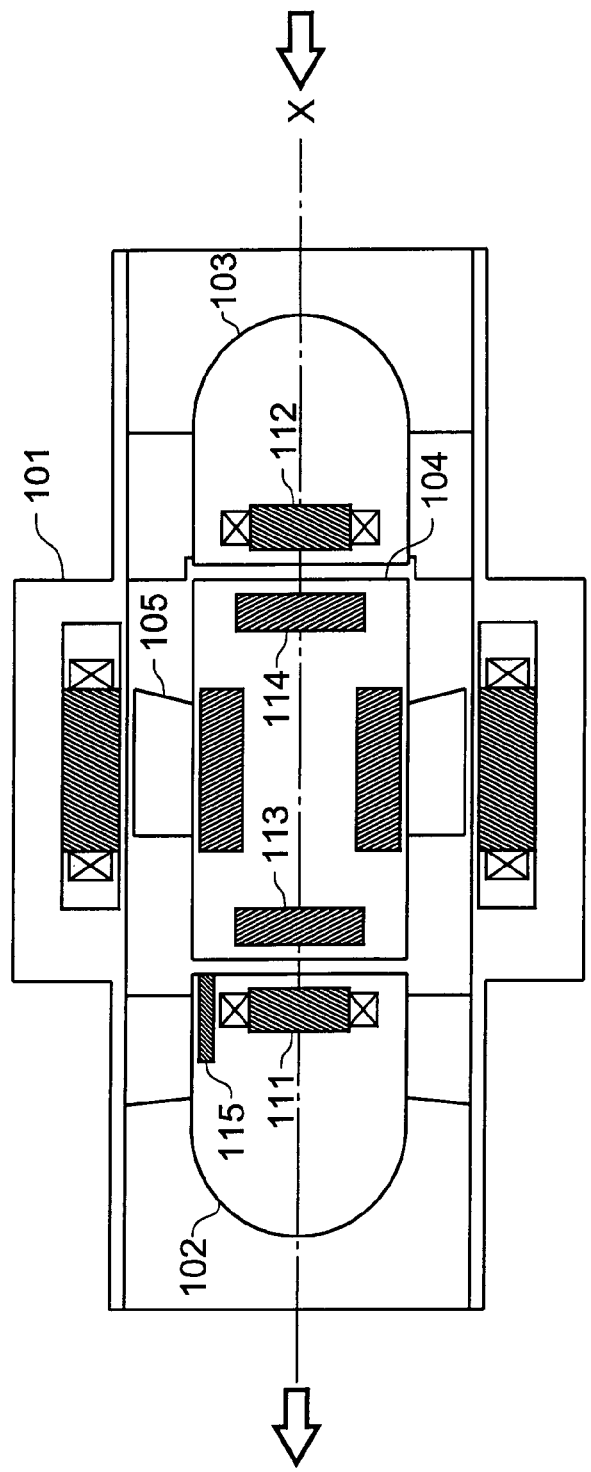
FIG. 15 is a cross-sectional view showing a construction of a conventional artificial heart pump employing active magnetic bearings.
Figure 16:
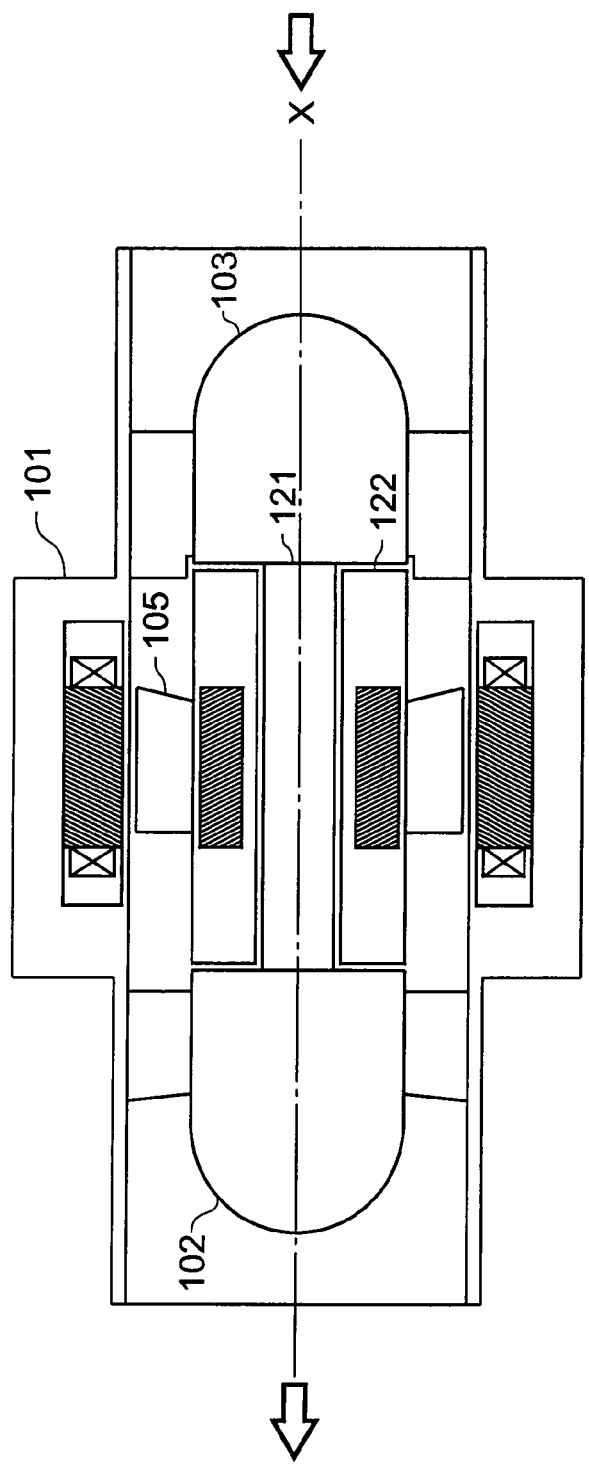
FIG. 16 is a cross-sectional view showing a construction of a conventional artificial heart pump employing hydrodynamic bearings.
Figure 17:
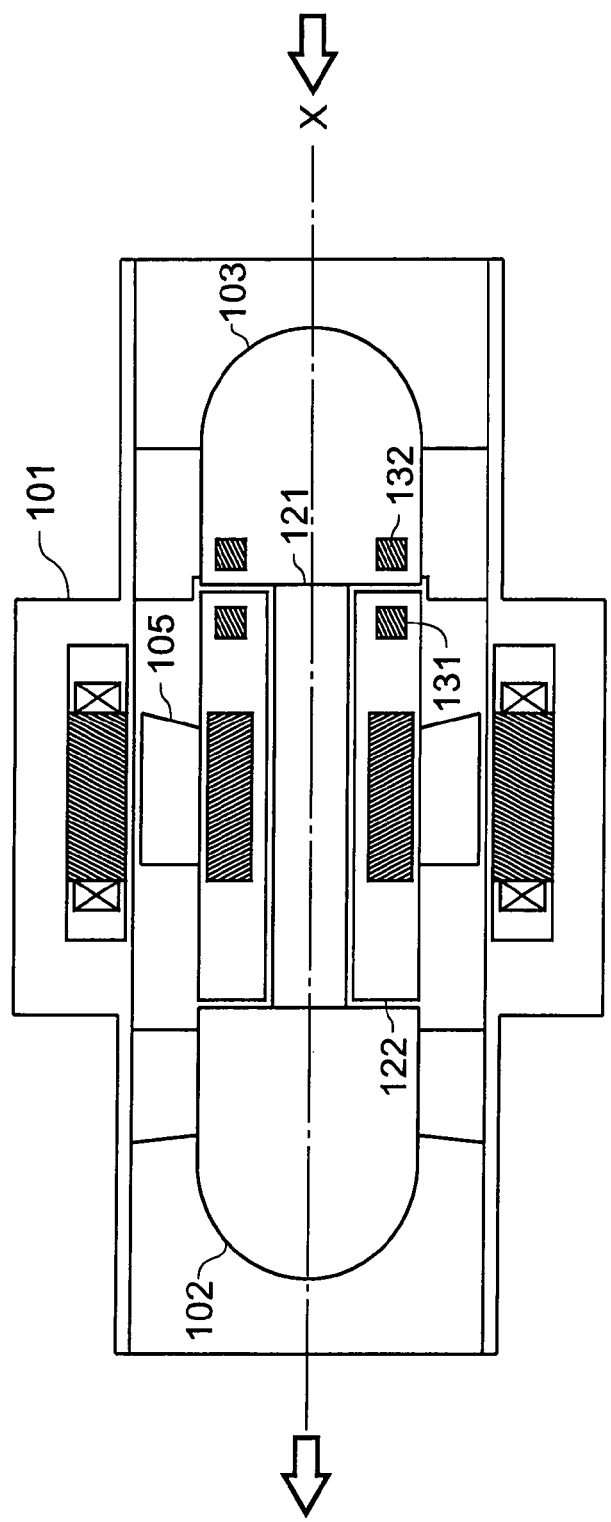
FIG. 17 is a cross-sectional view showing a construction of a conventional artificial heart pump employing passive type of repulsive magnetic bearings.

In order to secure a wide operation range for the artificial heart pump, there is a case in which the clearance between the sleeve 5 and either of the fixed bodies 3 and 8 is narrowed. Hereat, the hydrodynamic bearing by the thrust-hydrodynamic-pressure-generating grooves 100 as shown in FIG. 12 may be constructed only for the fixed body which has a narrower clearance to the sleeve. To be specific, for example, as shown in FIG. 13, when the clearance between the sleeve 5 and the fixed body 8 is broadened and the clearance between the sleeve 5 and the fixed body 3 is narrowed, in order to prevent the contact of the fixed body 3 with the sleeve 5, the thrust-hydrodynamic-pressure-generating grooves 100 as shown in FIG. 12 are formed only on the anterior end surface 3*x* of the fixed body 3. In addition, on the contrary, when the clearance between the sleeve 5 and the fixed body 3 is broadened and the clearance between the sleeve 5 and the fixed body 8 is narrowed, in order to prevent the contact of the fixed body 8 with the sleeve 5, the thrust-hydrodynamic-pressuregenerating grooves 100 as shown in FIG. 12 are formed only on the anterior end surface 8x of the fixed body 8.

Additionally, in the artificial heart pump being constructed in accordance with each of the above-mentioned embodiments, the hardness of the material constructing a rotating member that provides rotary drive, such as the sleeve 5, may be different from the hardness of the material constructing a fixed member that is fixed to the housing 1, such as the fixed bodies 3 and 8 and the fixed shaft 4. To be specific, for example, the material constructing the rotating member may be carbonitrided titanium alloy, and the material constructing the fixed members may be untreated titanium alloy. On the contrary, the material constructing the rotating member may be untreated titanium alloy, and the material constructing the fixed members may be carbonitrided titanium alloy. In order to carbonitride a member, the member is heated in the gas environment in which ammonia (NH3) is added to the carbonitrided gas being altered, such as natural gas, manufactured gas, propane, butane and the like, or added to the carbonitrided gas that is generated by dropping a liquid thereto.

As described hereinabove, because the fixed members and the rotating members are constructed of materials having different hardness, seizure can be prevented from occurring at the time of contact, so that the sliding characteristic thereof can be maintained as favorable. In addition, by applying the titanium alloy to the materials to be used for each portion, not only the biocompatibility thereof can be compensated but also the temperature of the environment can be lowered during treatment, by generating titanium alloys of different hardness as a result of the treatment by carbonitriding, and then, the thermal deformation of the members to be subject to the treatment can be restrained.

What is claimed is:

1. An artificial heart pump that moves blood fluid, comprising:
    a housing, which is a casing having a front-end with an inlet of the blood fluid and a rear-end with an outlet of the blood fluid;
    a fixed shaft, which has a cylindrical shape including a circumferential surface, a front-end surface facing toward the front-end of the housing, and a rear end surface facing toward the rear-end of the housing, and is fixed at a center position of the housing, with an axis thereof arranged in a direction parallel to a blood stream from the inlet to the outlet;
    a first fixed body, which is provided at the inlet side of the housing, having a larger diameter than the fixed shaft, and having a rear-end surface facing toward the rear-end of the housing, and further having a circumferential surface, and being fixed to the front-end surface of the fixed shaft in the middle of the rear-end surface of said first fixed body;
    a second fixed body, which is provided at the outlet side of the housing, having a larger diameter than the fixed shaft, and having a front-end surface facing toward the front-end of the housing and further having a circumferential surface, and being fixed to the rear-end surface of the fixed shaft in the middle of the front-end surface of said second fixed body;
    a rotating sleeve, which has a cylindrical tube shape, being positioned between the first and second fixed bodies, and having an outer circumferential surface, an inner circumferential surface surrounding an inner hole penetrated by the fixed shaft, a front-end surface facing toward the front-end of the housing, and a rear-end surface facing toward the rear-end of the housing;
    a plurality of impeller blades protruding radially from the outer circumferential surface of the rotating sleeve toward an inside wall of the housing;
    motor stators provided in the housing at suitable positions surrounding the rotating sleeve, which generate rotating magnetic fields inside the housing;
    permanent magnets, which are multi-polar and anistropic, being provided inside the rotating sleeve, generating a magnetic field perpendicular to the outer circumferential surface of the rotating sleeve;
    a first magnetic-field-generating portion, which is provided in one of the first and second fixed bodies, being positioned adjacent to the corresponding end surface of said one of the first and second fixed bodies, and which generates a magnetic field at the corresponding end surface of said one of the first and second fixed bodies;
    a second magnetic-field-generating portion, which is provided in the rotating sleeve, and positioned adjacent to one or more end surfaces thereof, and facing the corresponding end surface of the fixed body with the first magnetic-field-generating portion, and which generates a magnetic field perpendicular to the one or more end surfaces thereof;
    and an adjustment portion, which is installed between the corresponding end surface of the fixed body containing the first magnetic-field-generating portion and the corresponding end surface of the fixed shaft facing the corresponding end surface of the fixed body, and which adjusts a distance therebetween, thereby adjusting magnetic force between the first and second magnetic-field generating portions,
    wherein, the inner circumferential surface of the rotating sleeve is rotatably supported by the outer circumferential surface of the fixed shaft,
    wherein the first and second fixed bodies are installed in the housing by one of two alternative configurations:
    the first of said two alternative configurations is such that the circumferential surface of the first fixed body is bridged to the inside wall of the housing with a plurality of current plates, and the circumferential surface of the second fixed body is free of fixation to the inside wall of the housing and connected to the inside wall of the housing through the fixed shaft, the first fixed body, and the current plates;
    the second of said two alternative configurations is such that the circumferential surface of the second fixed body is bridged to the inside wall of the housing with a plurality of diffusers, and the circumferential surface of the first fixed body is free of fixation to the inside wall of the housing and connected to the inside wall of the housing through the fixed shaft, the second fixed body, and the diffusers,
    the first magnetic-field-generating portion is provided on the fixed body whose circumferential surface is free of fixation to the inside wall of the housing,
    the fixed body whose circumferential surface is free of fixation to the inside wall of the housing, is detachably connected to the corresponding end surface of the fixed shaft, and
    the magnetic fields generated by the first and the second magnetic-field-generating portions interact with each other, and contact between the fixed body containing the first magnetic-field-generating portion and the corresponding end-surface of the rotating sleeve facing the fixed body containing the first magnetic-field-generating portion is prevented by the interaction between the first and second magnetic-field-generating portions.

2. An artificial heart pump as described in claim 1,
wherein, the adjustment portion is a component which locates a position of the first magnetic-field-generating portion relative to the second magnetic-field-generating portion, by supplying a specific margin therebetween in the axial direction of the fixed shaft, and
the distance between the first and second magnetic-field-generating portion is adjusted by locating the position of the first magnetic-field generating portion with the component.

3. An artificial heart pump as described in claim 2,
wherein, a hardness of materials composing fixing members including the fixed bodies and the fixed shaft, is different from a hardness of materials composing rotating members including the rotating sleeve.

4. An artificial heart pump as described in claim 1 or claim 2,
wherein, the fixed body with the first magnetic-field-generating portion further comprises a protruding portion, which is in a cylindrical shape with a circumferential surface, provided on the middle of the corresponding end surface thereof protruding toward the fixed shaft,
the fixed shaft further comprises a hole, which is a recess penetrated by the protruding portion, at the corresponding end surface of the fixed shaft facing the fixed body with the first magnetic-field-generating portion, and the protruding portion is engaged into the hole of the fixed shaft, thereby connecting the fixed body with the first magnetic-field-generating portion and the fixed shaft.

5. An artificial heart pump as described in claim 4,
wherein, the adjustment portion includes one or more of a ring-shaped component with a hole,
the protruding portion of the fixed body penetrates through the hole of the ring-shaped component,
the end-surface of the fixed shaft facing the fixed body containing the first magnetic-field-generating portion, end-surfaces of the ring-shaped component, and the end-surface of the fixed body containing the first magnetic-field-generating portion, are firmly held together, and
a distance between the first and the second magnetic-field-generating portion is adjusted by changing a quantity of the ring-shaped components placed between the fixed body containing the first magnetic-field-generating portion and the fixed shaft.

6. An artificial heart pump as described in claim 1, further comprising:
thrust-hydrodynamic-pressure grooves formed on at least one of the end-surfaces of the first and second fixed bodies,
wherein, hydrodynamic pressure is generated by having a fluid flow into a space between the end-surface of the fixed body with the thrust-hydrodynamic-pressure grooves and the corresponding end surface of the rotating sleeve facing the end-surface of the fixed body with the thrust-hydrodynamic-pressure grooves.

7. An artificial heart pump as described in claim 1, further comprising:
a gap sensor in one of the first and second fixed bodies,
wherein, the gap sensor measures the distance between one of the end-surfaces of the fixed bodies and the corresponding end surface of the rotating sleeve facing thereto.

8. An artificial heart pump as described in claim 1,
wherein, the first and the second magnetic-field-generating portions are a pair of permanent magnets generating a repulsive magnetic force therebetween.

9. An artificial heart pump as described in claim 1
wherein, the first magnetic-field-generating portion is a magnetic body, and the second magnetic-field-generating portion is the multi-pole oriented anisotropic permanent magnet.

10. An artificial heart pump as described in claim 1,
wherein, a hardness of materials composing fixing members including the fixed bodies and the fixed shaft, is different from a hardness of materials composing rotating members including the rotating sleeve.

11. An artificial heart pump as described in claim 1,
wherein, the first fixed body is bridged to the inside wall of the housing with the current plates,
the second fixed body further comprises a plurality of diffusers on the circumferential surface thereof, and
outer edges of the diffusers are separated from the inside wall of the housing.

12. An artificial heart pump as described in claim 1,
wherein, the first fixed body is bridged to the inside wall of the housing with the current plates,
the inside wall of the housing further comprises a plurality of diffusers, which surround the second fixed body, and
outer edges of the diffusers are separated from the circumferential surface of the second fixed body.

13. An artificial heart pump as described in claim 1,
wherein, the second fixed body is bridged to the inside wall of the housing with the diffusers,
the first fixed body further comprises a plurality of current plates on the circumferential surface thereof, and
outer edges of the current plated are separated from the inside wall of the housing.

14. An artificial heart pump as described in claim 1,
wherein, the second fixed body is bridged to the inside wall of the housing with the diffusers,
the inside wall of the housing further comprises a plurality of current plates, which surround the first fixed body, and
outer edges of the current plates are separated from the circumferential surface of the first fixed body.

* * * * *